United States Patent
Speake

(10) Patent No.: US 10,239,885 B1
(45) Date of Patent: Mar. 26, 2019

(54) COMPOUND 1-[2-[4-(2-ETHYL-6,8-DIMETHYLIMIDAZO-[1,2-α]PYRAZIN-3-YL)PHENYL]ETHYL]-3-(P-TOLYLSULFONYL)UREA AS A PROSTAGLANDIN EP4 RECEPTOR ANTAGONIST

(71) Applicant: Avista Pharma Solutions, Inc., Durham, NC (US)

(72) Inventor: Jason D. Speake, Winston-Salem, NC (US)

(73) Assignee: Avista Pharma Solutions, Inc., Durham, NC (US)

( * ) Notice: Subject to any disclaimer, the term of this patent is extended or adjusted under 35 U.S.C. 154(b) by 0 days.

(21) Appl. No.: 16/100,315

(22) Filed: Aug. 10, 2018

Related U.S. Application Data

(60) Provisional application No. 62/686,299, filed on Jun. 18, 2018.

(51) Int. Cl.
   *A61K 31/4985* (2006.01)
   *C07D 487/04* (2006.01)

(52) U.S. Cl.
   CPC .................. *C07D 487/04* (2013.01)

(58) Field of Classification Search
   CPC .................. A61K 31/4985; C07D 487/04
   USPC .................. 514/249; 544/350
   See application file for complete search history.

(56) References Cited

U.S. PATENT DOCUMENTS

| | | |
|---|---|---|
| 2004/0220189 A1 | 11/2004 | Sun et al. |
| 2005/0009832 A1 | 1/2005 | Sun et al. |
| 2013/0195848 A1 | 8/2013 | Klar et al. |

FOREIGN PATENT DOCUMENTS

| | | |
|---|---|---|
| WO | 2002032422 A2 | 4/2002 |
| WO | 2002032900 A2 | 4/2002 |
| WO | 2003086371 A2 | 10/2003 |
| WO | 2006091671 A1 | 8/2006 |
| WO | 2006095268 A1 | 9/2006 |
| WO | 2011102149 A1 | 8/2011 |
| WO | 2011113862 A1 | 9/2011 |
| WO | 2011151259 A1 | 12/2011 |
| WO | 2014078813 A1 | 5/2014 |
| WO | 2014148053 A1 | 9/2014 |
| WO | 2018013430 A2 | 1/2018 |

OTHER PUBLICATIONS

Cruikshank et al.,"A Lipidated Anti-Tat Antibody Enters Living Cells and Blocks HIV-1 Viral Replication", J. Acquired Immune Deficiency Syndromes Hum. Retrovirol, Mar. 1997, vol. 14, pp. 193-203.

Cahn et al., "Specification of Molecular Chirality", Angew. Chem., Int. Ed. Engl. 1966, vol. 5, pp. 385-414.

Prelog and Helmchen, "Basic Principles of the CIP-System and Proposals for a Revision", Angew. Chem. Int. Ed. Engl., 1982, vol. 21, pp. 567-583.

Mata and Lobo, "The CIP Sequence Rules: Analysis and Proposal for a Revision", Tetrahedron: Asymmetry, 1993, vol. 4, pp. 657-668.

*Primary Examiner* — Douglas M Willis
(74) *Attorney, Agent, or Firm* — Brinks Gilson & Lione

(57) ABSTRACT

The present invention describes novel compounds, or veterinary or pharmaceutically acceptable salts thereof, veterinary or pharmaceutical compositions thereof, and medical uses thereof. The compounds of the invention have activity as prostaglandin EP4 receptor antagonists and are useful in the treatment or alleviation of pain, inflammation and inflammation-associated disorders. Also described herein are methods for treating pain by administering the compounds of the invention. For example, the invention describes 1-[2-[4-(2-ethyl-6,8-dimethylimidazo[1,2-a]pyrazin-3-yl)phenyl]ethyl]-3-(p-tolylsulfonyl)urea of the formula:

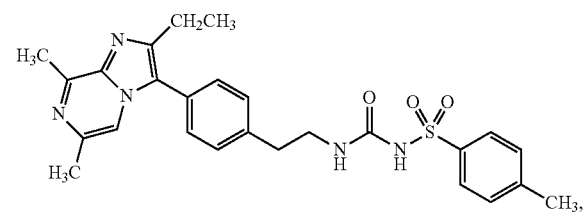

veterinary or pharmaceutical compositions thereof, and methods of treatment using the subject compound and compositions thereof.

2 Claims, No Drawings

COMPOUND 1-[2-[4-(2-ETHYL-6,8-DIMETHYLIMIDAZO-[1,2-α]PYRAZIN-3-YL)PHENYL]ETHYL]-3-(P-TOLYLSULFONYL)UREA AS A PROSTAGLANDIN EP4 RECEPTOR ANTAGONIST

RELATED APPLICATION

This application claims the benefit of U.S. Provisional Patent Application Ser. No. 62/686,299 filed Jun. 18, 2018, which is incorporated by reference in its entirety.

FIELD OF THE INVENTION

The present invention describes novel compounds, or their pharmaceutically acceptable salts, pharmaceutical compositions containing them, and their medical uses. The compounds of the invention have activity as prostaglandin EP4 receptor antagonists, and are useful in the treatment or alleviation of pain and inflammation and other inflammation-associated disorders, such as arthritis, treating or preventing disorders or medical conditions selected from pain, inflammatory diseases and the like. Also described herein are methods of treating pain by administering the compounds of the invention, which are EP4 receptor antagonists.

BACKGROUND

Rheumatoid arthritis (RA) is an immune-mediated, systemic inflammatory disease that affects mainly synovial joins, with intra-articular inflammation, synovial hyperplasia and progressive degradation of cartilage and bone. Prevalence of the disease is about 1% of the population, and the disease is more frequent (and perhaps worse) in women than in men. There have been clear advances in the pharmacological management of rheumatoid arthritis over the last decade, but many patients still do not tolerate or do not respond well to the available therapies.

Moreover, the control and management of arthritis associated pain and inflammation in animals, such as companion animals, specifically in dogs, is also an area of growing interest. Many FDA-approved drugs are available to treat pain associated with osteoarthritis (OA) in dogs (e.g., carprofen, firocoxib, meloxicam, deracoxib, and robenacoxib), all of which work by inhibiting cyclooxygenase enzymes. The FDA approved COX inhibitor NSAIDs for use in dogs, unless contra-indicated, are consider to be effective treatments for the pain associated with RA. These COX-inhibiting NSAIDs, as a class, however, carry the potential for adverse effects including gastrointestinal ulceration and perforation, and renal insufficiency. The Food and Drug Administration (FDA) has required language in the precaution section of the package inserts of these drugs warning that, as a class, they may be associated with renal, gastrointestinal (GI), and hepatic toxicity. Specifically, labels of these drugs warn of the "potential to produce GI ulceration and/or GI perforation".

Prostaglandins are mediators of pain, fever and other symptoms associated with inflammation. Especially prostaglandin E2 (PGE2) is the predominant eicosanoid detected in inflammation conditions. In addition, it is also involved in various physiological and/or pathological conditions and such as hyperalgesia, uterine contraction, digestive peristalsis, awakeness, suppression of gastric acid secretion, blood pressure, platelet function, bone metabolism, angiogenesis or the like.

Four PGE2 receptor subtypes (EP1, EP2, EP3 and EP4) displaying different pharmacological properties have been cloned. EP4 subtype, a Gs-coupled receptor stimulates cAMP production, and is distributed in a wide variety of tissue suggesting a major role in PGE2-mediated biological events.

Among the multiple targets involved in the pathogenesis of rheumatoid arthritis, the prostaglandin E2 receptor 4 (EP4) subtype receptor of prostaglandin E2 (PGE2) is one of the most promising because, unlike common NSAIDs that inhibit the synthesis of prostaglandins, selective EP4 antagonists have the potential to combine immunomodulatory and direct anti-inflammatory properties. Furthermore, the EP4 receptor in mice, humans and dogs has been cloned and characterized and the canine EP4 receptor has approximately 90% homology to the human receptor. EP4 antagonists present an opportunity for a novel pharmaceutical or veterinary therapy.

Grapiprant, whose chemical name is N-[[[2-[4-(2-Ethyl-4,6-dimethyl-1H-imidazo[4,5-c] pyridin-1-yl)phenyl]ethyl] amino]carbonyl]-4 methylbenzenesulfonamide, and sold under the tradename Galliprant®, is a prostaglandin E2 (PGE2) EP4 receptor antagonist; a non-cyclooxygenase (COX) inhibiting, non-steroidal anti-inflammatory drug (NSAID) in the piprant class. Grapiprant is indicated for the control of pain and inflammation associated with osteoarthritis (OA) in dogs. Further reference is made to WO 2002/032422, WO 2002/032900, WO 2006/095268, as well as WO 2003/086371, WO 2011/102149, and WO 2014/148053. Additional background research regarding compounds with an imidazopyridine or imidazopyrazine core ring structure include US 2013/195848, WO 2014/078813, WO 2011/151259, WO 2011/113862, US 2005/0009832, US 2004/0220189, WO 2006/091671, and WO 2018/013430. All of these cited patent publications are incorporated by reference with regard to their background teaching.

Despite this background of research and development, there remains a need for novel EP4 antagonists to offer safe and effective pharmaceutical or veterinary therapy.

SUMMARY

The present invention includes the compounds according to formula (I), or a veterinary or pharmaceutically acceptable salt thereof:

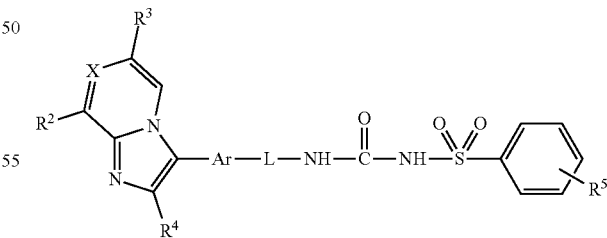

Formula (I)

wherein
X is N or $CR^1$, where each $R^1$ individually is hydrogen, halogen, CN, $C_{1-3}$ alkyl, or $C_{1-3}$ haloalkyl;
$R^2$ is hydrogen, $C_{1-3}$ alkyl, or $C_{1-3}$ haloalkyl;
$R^3$ is hydrogen, $C_{1-3}$ alkyl, or $C_{1-3}$ haloalkyl;
$R^4$ is hydrogen, $C_{1-3}$ alkyl, $C_{1-3}$ haloalkyl, or $C_{3-6}$ cycloalkyl;
$R^5$ is hydrogen, halogen, CN, $C_{1-3}$ alkyl, or $C_{1-3}$ haloalkyl;

Ar is phenyl, pyridyl, or thiophenyl, each optionally substituted with one or more halogen, CN, $NO_2$, $NH_2$, $N(C_{1-3}$ alkyl$)_2$, OH, $OC_{1-3}$ alkyl, $C_{1-3}$ alkyl, or $C_{1-3}$ haloalkyl; and L is —$CH_2CH_2$—, —$CH_2CH_2CH_2$—, or —$OCH_2CH_2$—.

As depicted, the group Ar may be attached to the imidazopyridine/pyrazine core and to the group L in any arrangement. In one embodiment, the imidazopyridine/pyrazine core is located para to the group L. In one embodiment, the group Ar is phenyl and the group L is arranged para to the imidazopyridine/pyrazine core; as will be appreciated, depending on numbering, namely a 1,4 arrangement. In one embodiment, the group Ar is pyridyl and the L group is arranged para to the imidazopyridine/pyrazine core; as will be appreciated, depending on numbering, namely a 2,5 or 3,6 arrangement. In one embodiment, the group Ar is thiophene and the group L is located, depending on numbering, namely a 2,4, 2,5, or 3,5 arrangement.

In one embodiment, the invention includes the compounds of formula (I) wherein X is N.

In one embodiment, the invention includes the compounds of formula (I) wherein $R^2$ is $C_{1-3}$ alkyl.

In one embodiment, the invention includes the compounds of formula (I) wherein $R^3$ is $C_{1-3}$ alkyl.

In one embodiment, the invention includes the compounds of formula (I) wherein $R^4$ is $C_{1-3}$ alkyl or $C_{1-3}$ haloalkyl.

In one embodiment, the invention includes the compounds of formula (I) wherein $R^5$ is $C_{1-3}$ alkyl or halogen.

In one embodiment, the invention includes the compounds of formula (I) wherein $R^5$ is $CH_3$, F, or Cl.

In one embodiment, the invention includes the compounds of formula (I) wherein Ar is phenyl. In a further aspect, Ar is phenyl and the L group is positioned para to the core imidazopyridine/pyrazine.

In one embodiment, the invention includes the compounds of formula (I) wherein Ar is phenyl, the group L is arranged para to the depicted core imidazopyridine/pyrazine, and Ar is either unsubstituted or substituted at one or more of the 2 and 3 positions.

In one embodiment, the invention includes the compounds of formula (I) wherein L is —$CH_2CH_2$—.

One embodiment of the present invention is a compound of the present invention selected from:
1-[2-[4-(2-ethyl-6,8-dimethyl-imidazo[1,2-a]pyrazin-3-yl)phenyl]ethyl]-3-(p-tolylsulfonyl) urea;
1-[2-[4-(7-cyano-2-ethyl-6,8-dimethyl-imidazo[1,2-a]pyridin-3-yl)phenyl]ethyl]-3-(p-tolylsulfonyl) urea;
1-[2-[4-(2-ethyl-7-fluoro-6,8-dimethyl-imidazo[1,2-a]pyridin-3-yl)phenyl]ethyl]-3-(p-tolylsulfonyl) urea;
1-[2-[4-(2-ethyl-6,8-dimethyl-imidazo[1,2-a]pyrazin-3-yl)phenoxy]ethyl]-3-(p-tolylsulfonyl)urea;
1-[2-[4-(2-ethyl-6,8-dimethyl-imidazo[1,2-a]pyrazin-3-yl)phenyl]-2-methyl-propyl]-3-(p-tolylsulfonyl) urea;
1-[[1-[4-(2-ethyl-6,8-dimethyl-imidazo[1,2-a]pyrazin-3-yl)phenyl]cyclopropyl]methyl]-3-(p-tolylsulfonyl) urea;
1-[2-[4-(2-ethyl-6,8-dimethyl-imidazo[1,2-a]pyrazin-3-yl)phenyl]ethyl]-3-(4-fluorophenyl) sulfonyl-urea;
1-[2-[4-(2-ethyl-6,8-dimethyl-imidazo[1,2-a]pyridin-3-yl)phenyl]ethyl]-3-(p-tolylsulfonyl) urea;
1-[2-[4-[6,8-dimethyl-2-(trifluoromethyl)imidazo[1,2-a]pyrazin-3-yl]phenyl]ethyl]-3-(p-tolylsulfonyl) urea; or
1-[2-[4-(2-cyclopropyl-6,8-dimethyl-imidazo[1,2-a]pyrazin-3-yl)phenyl]ethyl]-3-(p-tolylsulfonyl) urea;
or a veterinary or pharmaceutically acceptable salt thereof.

One embodiment of the invention includes compositions comprising a compound of Formula (I) and a pharmaceutically or veterinary acceptable carrier. The compositions of the invention can also be in a variety of forms which include, but are not limited to, oral formulations, injectable formulations, and topical, dermal, or subdermal formulations. The formulations are intended to be administered to an animal, which includes, but is not limited to, mammals, and birds. Examples of mammals include, but are not limited to, humans, cattle, sheep, goats, llamas, alpacas, pigs, horses, donkeys, dogs, cats, and other livestock or domestic mammals. Examples of birds include turkeys, chickens, ostriches, and other livestock or domestic birds.

Another embodiment of the present invention includes combination therapy, whereby one or more compounds of Formula (I) can be employed as such or in the form of their preparations or formulations as combinations with one or more other veterinary or pharmaceutically active substances, such as, for example, EP4 antisense nucleic acids, amino acids, peptides, carbohydrates, anti-EP4 antibodies, COX-2 selective, COX-1 selective or non-selective NSAIDs, opioids, local anesthetics, disease-modifying, anti-rheumatoid drugs, or steroids. The combinations may be part of the same formulation or may be administered separately or sequentially to the locus.

Another embodiment of the present invention includes a method for treating pain comprising administering to a subject in need thereof an effective amount of a compound of the present invention. Another embodiment of the present invention includes a compound of the present invention for use in therapy. Another embodiment of the present invention includes a compound of the present invention for the manufacture of a medicament for the treatment of pain. Another embodiment of the present invention includes use of a compound of the present invention for the treatment of pain. One aspect of these embodiments includes where the subject is a mammal. One aspect of these embodiments includes where the mammal is a companion animal. One aspect of these embodiments includes where the pain is associated with one or more of joint pain, musculoskeletal pain, lower back pain, neck pain, skeletal pain, sprain, strain, myositis, neuralgia, fibromyalgia, synovitis, arthritis, rheumatoid arthritis, degenerative joint disease, osteoarthritis, gout, ankylosing spondylitis, and bursitis.

One or more aspects and embodiments may be incorporated in a still further different embodiment. That is, all aspects and embodiments can be combined in any way or combination.

DETAILED DESCRIPTION

Definitions

When referring to the compounds disclosed herein, the following terms have the following meanings unless indicated otherwise. The following definitions are meant to clarify, but not limit, the terms defined. If a particular term used herein is not specifically defined, such term should not be considered indefinite. Rather, terms are used within their accepted meanings.

As used herein, "alkyl" refers to monovalent saturated aliphatic hydrocarbyl groups having from 1 to 20 carbon atoms, preferably 1-8 carbon atoms, preferably 1-6 carbon atoms. The hydrocarbon chain can be either straight-chained or branched. Illustrative alkyl groups include methyl, ethyl, n-propyl, isopropyl, n-butyl, iso-butyl, and tert-butyl. Similarly, an "alkenyl" group refers to an alkyl group having one or more double bonds present in the chain.

As used herein, "cycloalkyl" refers to an unsaturated or partially saturated hydrocarbon ring, containing from 3 to 6 ring atoms. Illustrative cycloalkyl groups include cyclopropyl, cyclobutyl, cyclopentyl, cyclohexyl, as well as partially saturated versions thereof, such as cyclohexenyl, and cyclohexadienyl.

As used herein "halogen" or "halo" refers to a halogen. In some embodiments, the halogen is preferably Br, Cl, or F.

As used herein, "haloalkyl" refers to monovalent saturated aliphatic hydrocarbyl groups having from 1 to 20 carbon atoms, preferably 1-8 carbon atoms, preferably 1-6 carbon atoms, wherein at least one hydrogen atom is substituted by a halogen, including but not limited to perhalo groups where all hydrogen atoms are replaced with halogen atoms. The haloalkyl chain can be either straight-chained or branched. Illustrative alkyl groups include trifluoromethyl, trichloromethyl, trifluoroethyl, trifluoropropyl, trifluorobutyl, and pentafluoroethyl. Similarly, a "haloalkenyl" group refers to a haloalkyl group having one or more double bonds present in the chain.

As used herein "optionally substituted" refers to a substitution of a hydrogen atom, which would otherwise be present on the substituent. When discussing ring systems, the optional substitution is typically with 1, 2, or 3 substituents replacing the normally-present hydrogen. When referencing straight and branched moieties, however, the number of substitutions can be more, occurring wherever hydrogen is usually present. The substitutions can be the same or different. Illustrative substitutions include nitro, —NR'R", cyano, —NR'COR''', alkyl, alkenyl, —C(O), —SO$_2$R''', —NR'SO$_2$R''', —SO$_2$NR'R", —CONR'R", —CONHC$_6$H$_5$, hydroxy, alkoxy, alkylsulfonyl, haloalkyl, haloalkenyl, haloalkoxy, mercapto (—SH), thioalkyl, halogen, cycloalkyl, heterocyclyl, aryl, or heteroaryl, as each is understood in the art, and where R' and R" are the same or different and each represents hydrogen or alkyl; or when R' and R" are each attached to a nitrogen atom, they may form a saturated or unsaturated heterocyclic ring containing from 4 to 6 ring atoms, and wherein R" is alkyl or haloalkyl.

As used herein the phrase veterinary or veterinarily, or pharmaceutical or pharmaceutically acceptable salt refers to any salt of a compound disclosed herein which retains its biological properties and which is not toxic or otherwise undesirable for veterinary or pharmaceutical use. Such salts may be derived from a variety of organic and inorganic counter-ions known in the art. Such salts include acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid, and like acids.

Salts further include, by way of example only, salts of non-toxic organic or inorganic acids, such as halides, such as, chloride and bromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate, and the like.

Examples of inorganic bases that can be used to form base addition salts include, but are not limited to, metal hydroxides, such as lithium hydroxide, sodium hydroxide, and potassium hydroxide; metal amides, such as lithium amide and sodium amide; metal carbonates, such as lithium carbonate, sodium carbonate, and potassium carbonate; and ammonium bases such as ammonium hydroxide and ammonium carbonate.

Examples of organic bases that can be used to form base addition salts include, but are not limited to, metal alkoxides, such as lithium, sodium, and potassium alkoxides including lithium methoxide, sodium methoxide, potassium methoxide, lithium ethoxide, sodium ethoxide, potassium ethoxide, and potassium tert-butoxide; quaternary ammonium hydroxides, such as choline hydroxide; and amines including, but not limited to, aliphatic amines (i.e., alkylamines, alkenylamines, alkynylamines, and alicyclic amines), heterocyclic amines, arylamines, heteroarylamines, basic amino acids, amino sugars, and polyamines.

According to embodiments of the present invention, the base can be a quaternary ammonium hydroxide, wherein one or more of the alkyl groups of the quaternary ammonium ion are optionally substituted with one or more suitable substituents. Preferably, at least one alkyl group is substituted with one or more hydroxyl groups. Non-limiting examples of quaternary ammonium hydroxides that can be used in accordance with the present invention include choline hydroxide, trimethylethylammonium hydroxide, tetramethylammonium hydroxide, and is preferably choline hydroxide. According to embodiments of the present invention, an alkylamine base can be substituted or unsubstituted. Non-limiting examples of unsubstituted alkylamine bases that can be used in accordance with the present invention include methylamine, ethylamine, diethylamine, and triethylamine. A substituted alkylamine base is preferably substituted with one or more hydroxyl groups; and preferably one to three hydroxyl groups. Non-limiting examples of substituted alkylamine bases that can be used in accordance with the present invention include 2-(diethylamino)ethanol, INN-dimethylethanolamine (deanol), tromethamine, ethanolamine, and diolamine.

In certain cases, the depicted substituents can contribute to optical and/or stereoisomerism. Compounds having the same molecular formula but differing in the nature or sequence of bonding of their atoms or in the arrangement of their atoms in space are termed "isomers." Isomers that differ in the arrangement of their atoms in space are termed "stereoisomers." Stereoisomers that are not mirror images of one another are termed "diastereomers" and those that are non-superimposable mirror images of each other are termed "enantiomers". When a compound has an asymmetric center, for example when it is bonded to four different groups, a pair of enantiomers is possible. An enantiomer can be characterized by the absolute configuration of its asymmetric center and is designated (R) or (S) according to the rules of Cahn and Prelog (Cahn et al., 1966, *Angew. Chem.* 78: 413-447, *Angew. Chem., Int. Ed. Engl.* 5: 385-414 (errata: *Angew. Chem., Int. Ed. Engl.* 5:511); Prelog and Helmchen, 1982, *Angew. Chem.* 94: 614-631, *Angew. Chem. Internat. Ed. Eng.* 21: 567-583; Mata and Lobo, 1993, *Tetrahedron: Asymmetry* 4: 657-668) or can be characterized by the manner in which the molecule rotates the plane of polarized light and is designated dextrorotatory or levorotatory (namely, as (+)- or (−)-isomers, respectively). A chiral compound can exist as either an individual enantiomer or as a mixture thereof. A mixture containing equal proportions of enantiomers is called a "racemic mixture".

In certain embodiments, the compounds disclosed herein can possess one or more asymmetric centers; and such compounds can therefore be produced as the individual (R)- or (S)-enantiomer or as a mixture thereof. Unless indicated otherwise, for example by designation of stereochemistry at any position of a formula, the description or naming of a particular compound in the specification and claims is intended to include both individual enantiomers and mixtures, racemic or otherwise, thereof. Methods for determination of stereochemistry and separation of stereoisomers are well-known in the art.

In certain embodiments, the compounds disclosed herein are "stereochemically pure". A stereochemically pure compound has a level of stereochemical purity that would be recognized as "pure" by those of skill in the art. Of course, this level of purity may be less than 100%. In certain embodiments, "stereochemically pure" designates a compound that is substantially free, i.e. at least about 85% or more, of alternate isomers. In particular embodiments, the compound is at least about 85%, about 90%, about 91%, about 92%, about 93%, about 94%, about 95%, about 96%, about 97%, about 98%, about 99%, about 99.5% or about 99.9% free of other isomers.

As used herein, the terms "subject" and "patient" are used interchangeably herein. The terms "subject" and "subjects" refer to a human. In one embodiment, the subject is a companion animal such as a dog or cat. In a further embodiment the subject is an animal of agricultural importance such as a sheep, cow, horse, goat, fish, pig, or domestic fowl (such as a chicken, turkey, duck, or goose). In another embodiment the subject is a primate such as a monkey such as a cynomolgous monkey, a chimpanzee, and a human or non-primate animal.

In addition, a pharmaceutically acceptable prodrug of the compound represented by the formula (I) is also included in the present invention. The pharmaceutically acceptable prodrug refers to a compound having a group which can be converted into an amino group, a hydroxyl group, a carboxyl group, or the like, by solvolysis or under a physiological condition. Examples of the groups forming the prodrug include those as described in Prog. Med., 5, 2157-2161 (1985) or "Pharmaceutical Research and Development" (Hirokawa Publishing Company, 1990), vol. 7, Drug Design, 163-198. The term prodrug is used throughout the specification to describe any pharmaceutically acceptable form of a compound which, upon administration to a patient, provides the active compound. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

The present invention includes all pharmaceutically acceptable isotopically-labelled compounds of the invention wherein one or more atoms are replaced by atoms having the same atomic number, but an atomic mass or mass number different from the atomic mass or mass number usually found in nature. Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S. Certain isotopically-labelled compounds of the invention, such as those incorporating a radioactive isotope, may be useful in drug or substrate tissue distribution studies. The radioactive isotopes tritium, i.e. $^3$H, and carbon-14, i.e. $^{14}$C, are particularly useful for this purpose in view of their ease of incorporation and ready means of detection. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of the invention can generally be prepared by conventional techniques known to those skilled in the art or by processes analogous to those described in the accompanying Examples and Preparations using an appropriate isotopically-labeled reagent in place of the non-labeled reagent previously employed.

Synthesis

Generally the compounds of the invention can be prepared, isolated or obtained by any method apparent to those of skill in the art. Exemplary methods of preparation are illustrated by the following schemes.

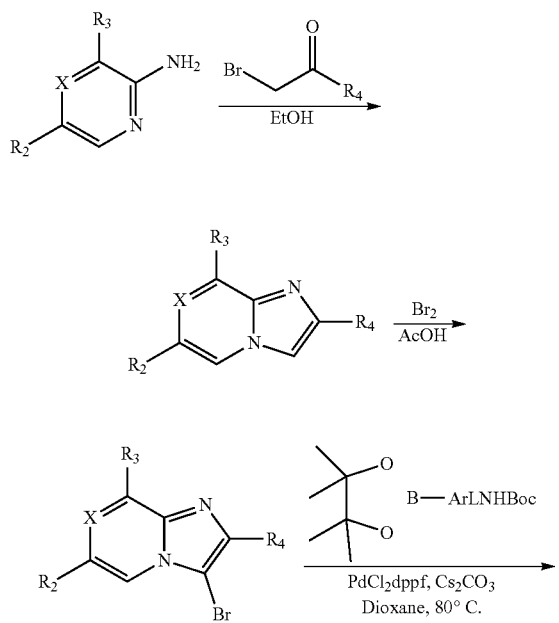

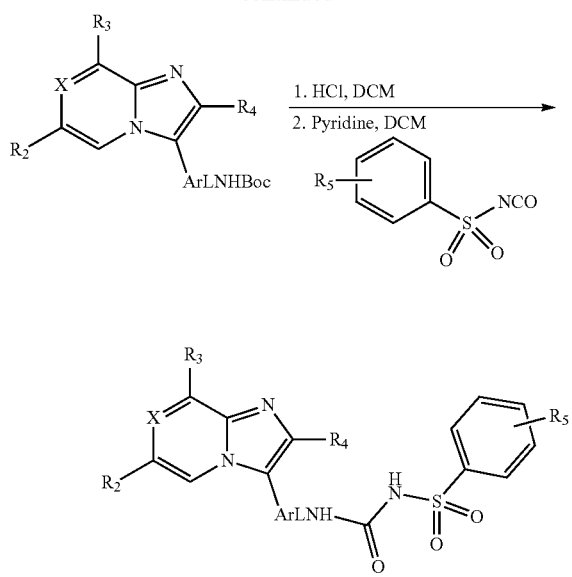

Alternatively, compounds of the present invention can be formed according to the below scheme, involving palladium coupling a fully elaborated boronic acid derivative, rather than generating a Boc protected intermediate:

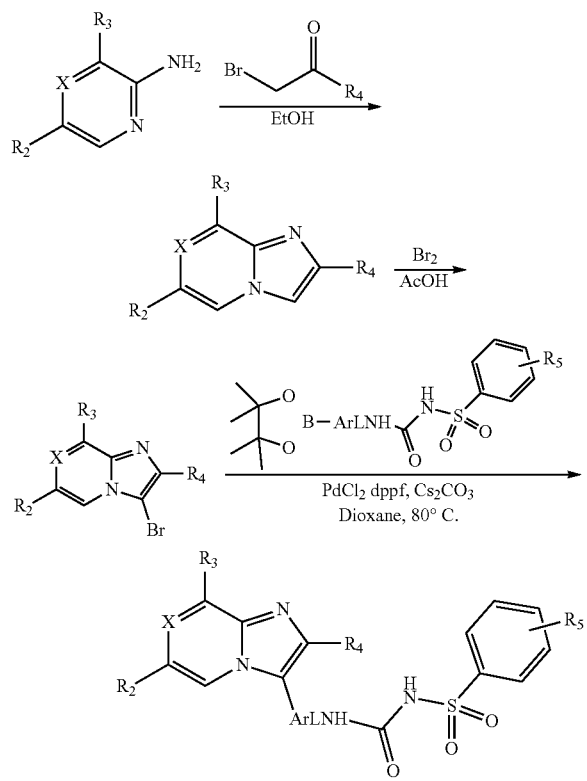

Alternatively, compounds of the present invention can be formed according to the below scheme, involving the formation of the imidazopyridine or imidazopyrazine ring with the Ar-L-N already installed, then further elaboration to the desired compounds:

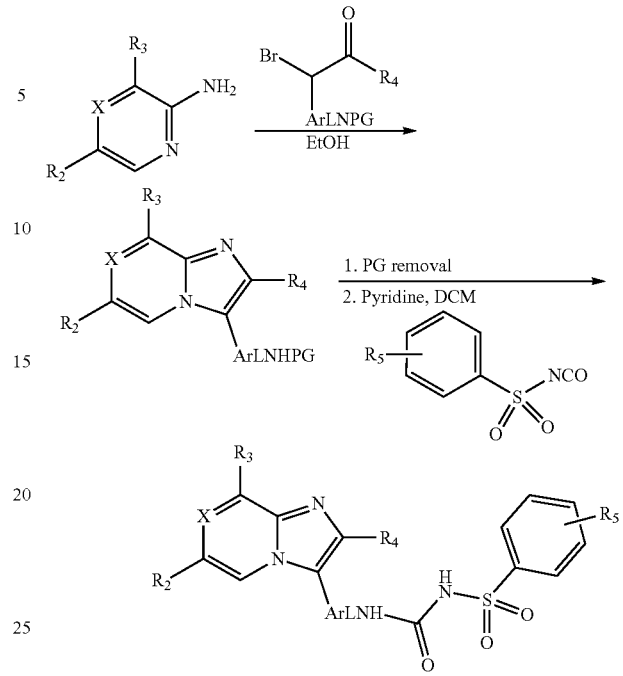

Compositions and Methods of Administration

The compounds of formula (I) used in the methods disclosed herein can be administered in certain embodiments using veterinary or pharmaceutical compositions including at least one compound of formula (I), if appropriate in the salt form, either used alone or in the form of a combination with one or more compatible and veterinary or pharmaceutically acceptable carriers, such as diluents or adjuvants, or with another agent. There are provided compositions which comprise a derivative of formula (I) or a salt thereof, and an acceptable excipient, carrier or diluent. The composition can also be in a variety of forms which include, but are not limited to, oral formulations, injectable formulations, and topical, dermal or subdermal formulations.

The composition can be in a form suitable for oral use, for example, as dietary supplements, troches, lozenges, chewables, tablets, hard or soft capsules, emulsions, aqueous or oily suspensions, aqueous or oily solutions, dispersible powders or granules, syrups, or elixirs. Compositions intended for oral use can be prepared according to any method known in the art for the manufacture of veterinary or pharmaceutical compositions and such compositions can contain one or more agents selected from the group consisting of sweetening agents, bittering agents, flavoring agents, coloring agents and preserving agents in order to provide elegant and palatable preparations.

Lozenges are solid compositions containing one or more active ingredients intended to dissolve or disintegrate slowly in the oral cavity by passive incubation in the oral cavity, or actively by sucking or chewing. They can be used for systemic effect if the drug is absorbed through the buccal or esophageal lining or is swallowed. In particular, soft lozenges can be chewed or allowed to dissolve slowly in the mouth. These dosage forms have the advantage of being flavored and thus easy to administer to both human and animal patients; have formulas that are easy to change and can be patient specific; can deliver accurate amounts of the active ingredient to the oral cavity and digestive system; and allow for the drug to remain in contact with the oral or esophageal cavity for an extended period of time.

Tablets can contain the active ingredient in admixture with non-toxic, pharmaceutically acceptable excipients which are suitable for the manufacture of tablets. These excipients can be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period.

Formulations for oral use can be hard gelatin capsules, wherein the active ingredient is mixed with an inert solid diluent, for example, calcium carbonate, calcium phosphate or kaolin. Capsules can also be soft gelatin capsules, wherein the active ingredient is mixed with water or miscible solvents such as propylene glycol, PEGs and ethanol, or an oil medium, for example, peanut oil, liquid paraffin, or olive oil.

The compositions can also be in the form of oil-in-water or water-in-oil emulsions. The oily phase can be a vegetable oil, for example, olive oil or *arachis* oil, or a mineral oil, for example, liquid paraffin or mixtures of these. Suitable emulsifying agents may be naturally-occurring phosphatides, for example, soy bean, lecithin, and esters or partial esters derived from fatty acids and hexitol anhydrides, for example, sorbitan monoleate, and condensation products of the said partial esters with ethylene oxide, for example, polyoxyethylene sorbitan monooleate. The emulsions can also contain sweetening agents, bittering agents, flavoring agents, and preservatives.

In one embodiment of the formulation, the composition is in the form of a microemulsion. Microemulsions are well suited as the liquid carrier vehicle. Microemulsions are quaternary systems comprising an aqueous phase, an oily phase, a surfactant and a cosurfactant. They are translucent and isotropic liquids. Microemulsions are composed of stable dispersions of microdroplets of the aqueous phase in the oily phase or conversely of microdroplets of the oily phase in the aqueous phase. The size of these microdroplets is less than 200 nm (1000 to 100,000 nm for emulsions). The interfacial film is composed of an alternation of surface-active (SA) and co-surface-active (Co-SA) molecules which, by lowering the interfacial tension, allows the microemulsion to be formed spontaneously. In one embodiment of the oily phase, the oily phase can be formed from mineral or vegetable oils, from unsaturated polyglycosylated glycerides or from triglycerides, or alternatively from mixtures of such compounds. In one embodiment of the oily phase, the oily phase comprises of triglycerides; in another embodiment of the oily phase, the triglycerides are medium-chain triglycerides, for example, $C_8$-$C_{10}$ caprylic/capric triglyceride. In another embodiment, the oily phase will represent a % v/v range selected from the group consisting of about 2 to about 15%; about 7 to about 10%; and about 8 to about 9% v/v of the microemulsion. The aqueous phase includes, for example, water or glycol derivatives, such as propylene glycol, glycol ethers, polyethylene glycols or glycerol. In one embodiment of the glycol derivatives, the glycol is selected from the group consisting of propylene glycol, diethylene glycol monoethyl ether, dipropylene glycol monoethyl ether and mixtures thereof. Generally, the aqueous phase will represent a proportion from about 1 to about 4% v/v in the microemulsion. Surfactants for the microemulsion include diethylene glycol monoethyl ether, dipropylene glycol monomethyl ether, polyglycolyzed $C_8$-$C_{10}$ glycerides or polyglyceryl-6 dioleate. In addition to these surfactants, the cosurfactants include short-chain alcohols, such as ethanol and propanol. Some compounds are common to the three components discussed above, for example, aqueous phase, surfactant and cosurfactant. However, it is well within the skill level of the practitioner to use different compounds for each component of the same formulation. In one embodiment for the amount of surfactant/cosurfactant, the cosurfactant to surfactant ratio will be from about 1/7 to about 1/2.

In another embodiment for the amount of cosurfactant, there will be from about 25 to about 75% v/v of surfactant and from about 10 to about 55% v/v of cosurfactant in the microemulsion.

Oily suspensions can be formulated by suspending the active ingredient in a vegetable oil, for example, atachis oil, olive oil, sesame oil or coconut oil, or in mineral oil such as liquid paraffin. The oily suspensions can contain a thickening agent, for example, beeswax, hard paraffin or cetyl alcohol. Sweetening agents such as sucrose, saccharin or aspartame, bittering agents, and flavoring agents can be added to provide a palatable oral preparation. These compositions can be preserved by the addition of an anti-oxidant such as ascorbic acid, or other known preservatives.

Aqueous suspensions can contain the active material in admixture with excipients suitable for the manufacture of aqueous suspensions. Such excipients are suspending agents, for example, sodium carboxymethylcellulose, methylcellulose, hydroxypropylmethylcellulose, sodium alginate, polvinylpyrrolidone, gum tragacanth and gum acacia; dispersing or wetting agents can be a naturally-occuring phosphatide, for example, lecithin, or condensation products of an alkylene oxide with fatty acids, for example, polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide, with partial esters derived from fatty acids and hexitol anhydrides, for example, polyethylene sorbitan monooleate. The aqueous suspensions can also contain one or more preservatives, for example, ethyl, or n-propyl, p-hydroxybenzoate, one or more coloring agents, one or more flavoring agents, and one or more sweetening agents and/or bittering agents, such as those set forth above.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, bittering, flavoring and coloring agents, can also be present.

Syrups and elixirs can be formulated with sweetening agents, for example, glycerol, propylene glycol, sorbitol or sucrose. Such formulations may also contain a demulcent, a preservative, flavoring agent(s) and coloring agent(s).

The compositions can be in the form of a sterile injectable aqueous or oleagenous suspension. This suspension can be formulated according to the known art using those suitable dispersing or wetting agents and suspending agents which have been mentioned above. The sterile injectable preparation can also be a sterile injectable solution or suspension in a non-toxic parenterally-acceptable diluent or solvent, for example, as a solution in 1,3-butane diol. Among the acceptable vehicles and solvents that can be employed are water, Ringer's solution and isotonic sodium chloride solution. Cosolvents such as ethanol, propylene glycol or polyethylene glycols can also be used. Preservatives, such as phenol or benzyl alcohol, can be used.

In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables.

Topical, dermal and subdermal formulations can include emulsions, creams, ointments, gels or pastes.

Organic solvents that can be used in the invention include but are not limited to: acetyltributyl citrate, fatty acid esters such as the dimethyl ester, diisobutyl adipate, acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone (e.g. N-methylpyrrolidone), diethylene glycol monoethyl ether, ethylene glycol and diethyl phthalate, or a mixture of at least two of these solvents.

As vehicle or diluent, compositions of the present invention may include plant oils such as, but not limited to soybean oil, groundnut oil, castor oil, corn oil, cotton oil, olive oil, grape seed oil, sunflower oil, etc.; mineral oils such as, but not limited to, petrolatum, paraffin, silicone, etc.; aliphatic or cyclic hydrocarbons or alternatively, for example, medium-chain (such as $C_8$-$C_{12}$) triglycerides.

Dosage forms can contain from about 0.5 mg to about 5 g of an active agent.

In one embodiment of the invention, the active agent is present in the formulation at a concentration of about 0.05 to 10% weight/volume.

The compounds of formula (I) can be employed as such or in the form of their preparations or formulations as combinations The compounds of formula (I) according to the invention may be combined with one or more agents having the same sphere of activity, for example, to increase activity, or with substances having another sphere of activity, for example, to broaden the range of activity. The compounds of formula (I) have been found to possess activity as prostaglandin E2 receptor antagonist, preferably as EP4 receptor antagonists. Thus, the compounds of the present invention may also be combined with other agents that inhibit EP4 activity. Such EP4 inhibitors can include small molecules, nucleic acids, e.g., EP4 antisense nucleic acids, amino acids, peptides, carbohydrates, and anti-EP4 antibodies. Preferably, such agents are combined with a pharmaceutically acceptable delivery vehicle or carrier. Examples of EP4 antibodies include, for example, polyclonal, monoclonal, humanized, anti-idiotypic, chimeric or single chain antibodies, Fab, F(ab')$_2$, and Fab expression library fragments, scFV molecules, and epitope-binding fragments thereof. An antisense oligonucleotide directed to the EP4 gene or mRNA to inhibit its expression is made according to standard techniques (see, e.g., Agrawal et al., *Methods in Molecular Biology: Protocols for Oligonucleotides and Analogs*, Vol. 20, (1993)).

For anti-EP4 antibodies, the preferred dosage is generally 0.2 mg/kg to 20 mg/kg body weight. Generally, partially humanized antibodies and fully human antibodies have a longer half-life within the human body than other antibodies. Accordingly, lower dosages and less frequent administration are possible. Modifications such as lipidation can be used to stabilize antibodies and to enhance uptake and tissue penetration. A method for lipidation of antibodies is described in Cruikshank et al., *J. Acquired Immune Deficiency Syndromes Hum. Retrovirol.* 14: 193, (1997).

The compounds of formula (I) may also be co-administered with a COX-2 selective NSAID. Further, the present invention also encompasses a pharmaceutical composition for the treatment of inflammation, rheumatoid arthritis, pain, common cold, osteoarthritis, neuropathic pain, brain tumor, diuresis, or the like, which comprises a therapeutically effective amount the aryl or heteroaryl fused imidazole compound of formula (I) and a COX-2 selective NSAID or their veterinary or pharmaceutically acceptable salt together with a veterinary or pharmaceutically acceptable carrier.

The compounds of the invention may advantageously be employed in combination with one or more other therapeutic ingredients selected from a COX-2 selective NSAID, COX-1 selective NSAID, non-selective NSAIDs, opioids, anticonvulsants, antidepressants, local anesthetics, disease-modifying anti-rheumatoid drugs, or steroids.

The combination with a COX-2 selective NSAID is particularly favored for use in the prophylaxis and treatment of pain and arthritis. Examples of a COX-2 selective NSAID are nimesulide, celecoxib, rofecoxib, firocoxib and valdecoxib.

The pharmaceutical preparation comprising the compounds of formula (I), for delivery to a human or other mammal, is preferably in unit dosage form, in which the preparation is subdivided into unit doses containing an appropriate quantity of the active component. The unit dosage form can be a packaged preparation containing discrete quantities of the preparation, such as packaged tablets, capsules, and powders in vials or ampoules. Also, the unit dosage form can be a capsule, tablet or lozenge itself, or it can be an appropriate number of any of these in packaged form.

The quantity of active component in a unit dose preparation can be varied or adjusted from about 0.1 mg to about 1000 mg, according to the particular application and the potency of the active component. The composition can, if desired, also contain other compatible therapeutic agents.

In therapeutic use for the treatment or prevention of pain or inflammation in a human or other mammal, the compounds utilized in the method of treatment are administered at an initial dosage of about 0.1 mg/kg to about 100 mg/kg per interval. Preferred intervals may be daily, weekly, monthly, quarterly, semi-annually, or annually. The dosages can be varied depending on the requirements of the patient, for example, the size of the human or mammal being treated, the severity of the condition being treated, the route of administration, and the potency of the compound(s) being used. Determination of the proper dosage and route of administration for a particular situation is within the skill of the practitioner. Generally, the treatment will be initiated with smaller dosages, which are less than the optimum dose of the compound, which can be increased in small increments until the optimum effect under the particular circumstances of the infection is reached. For convenience, the total daily dosage can be divided and administered in portions during the day if desired.

In therapeutic use, the compounds of formula (I) are useful in manufacture of a medicament for a method of the treating of pain associated with rheumatic fever, influenza or other viral infections, common cold, lower back and neck pain, skeletal pain, postpartum pain, dysmenorrhea, headache, migraine, toothache, sprains and strains, myositis, neuralgia, fibromyalgia, synovitis, arthritis, including rheumatoid arthritis, degenerative joint disease (osteoarthritis), gout and ankylosing spondylitis, bursitis, burns including radiation and corrosive chemical injuries, sunburns, pain following surgical and dental procedures or bone fracture, immune and autoimmune diseases such as systemic lupus erythematosus; AIDS (acquired immune deficiency syndrome), gastrointestinal cancers such as colon cancer; cellular neoplastic transformations or metastatic tumor growth; diabetic retinopathy, tumor angiogenesis, prostanoid-induced smooth muscle contraction associated with dysmenorrhea, premature labor, allergic rhinitis, atopic dermatitis, asthma or eosinophil related disorders, hyperimmunoglobulinaemia, Castleman's disease, myeloma; Alzheimer's disease, sleep disorders, endocrine disturbance, glaucoma, bone loss; osteoporosis; promotion of bone formation, Paget's disease; cyto-protection in peptic ulcers, gastritis, regional enteritis, ulcerative colitis, diverticulitis or other gastrointestinal lesions; GI bleeding and patients undergoing chemotherapy; coagulation disorders selected from hypoprothrombinemia, hemophilia and other bleeding problems; kidney disease; thrombosis; occlusive vascular disease; pre-surgery; and anti-coagulation, or the like in mammals, especially humans, dogs and cats.

The compounds of formula (I) may, in particular, be used in the fields of veterinary medicine, livestock husbandry and in particular, warm-blooded vertebrates, including companion animals such as dogs and cats, horses, livestock, and fowl.

The compounds of the present invention, stereoisomers thereof, and veterinary or pharmaceutically acceptable salts thereof, and compositions comprising compounds of the present invention in conjunction with at least one other veterinary agent are of particular value in the control of pain and inflammation in companion animals, particularly dogs and cats, livestock and birds.

Any of the compounds of the present invention, or a suitable combination of a compound of the present invention and optionally, with at least one additional veterinary agent may be administered directly to the animal and/or indirectly by applying it to the local environment in which the animal dwells (such as bedding, enclosures, and the like). Direct administration includes contacting the skin, fur, or feathers of a subject animal with the compound(s), or by feeding or injecting the compounds into the animal.

The Formula (I) compound, stereoisomer thereof, and veterinary acceptable salt thereof, and combinations with at least one additional veterinary agent, as described herein, are believed to be of value for the treatment and control of the various symptoms associated with arthritis, including pain and inflammation.

The present invention also relates to a method of administering a compound of the present invention alone or in combination with at least one additional veterinary agent, and optionally a veterinary acceptable excipient, diluent, or carrier, to animals in good health comprising the application to said animal to reduce or eliminate the pain and inflammation due to various forms of arthritis.

The present invention explicitly encompasses those compounds presented in Table 1. A composition comprising a therapeutically acceptable amount of any of these compounds is also within the scope of the invention. The composition can further comprise a veterinary acceptable excipient, diluent, carrier, or mixture thereof. Such a composition can be administered to an animal in need thereof to treat and/or prevent a parasitic infection or infestation. The composition can further comprise an additional veterinary agent, as described herein.

TABLE 1

| Ref. No. | Compound Name |
|---|---|
| 1 | 1-[2-[4-(2-ethyl-6,8-dimethyl-imidazo[1,2-a]pyrazin-3-yl)phenyl]ethyl]-3-(p-tolylsulfonyl)urea |
| 2 | 1-[2-[4-(7-cyano-2-ethyl-6,8-dimethyl-imidazo[1,2-a]pyridin-3-yl)phenyl]ethyl]-3-(p-tolylsulfonyl)urea |
| 3 | 1-[2-[4-(2-ethyl-7-fluoro-6,8-dimethyl-imidazo[1,2-a]pyridin-3-yl)phenyl]ethyl]-3-(p-tolylsulfonyl)urea |
| 4 | 1-[2-[4-(2-ethyl-6,8-dimethyl-imidazo[1,2-a]pyrazin-3-yl)phenoxy]ethyl]-3-(p-tolylsulfonyl)urea |
| 5 | 1-[2-[4-(2-ethyl-6,8-dimethyl-imidazo[1,2-a]pyrazin-3-yl)phenyl]-2-methyl-propyl]-3-(p-tolylsulfonyl)urea |
| 6 | 1-[[1-[4-(2-ethyl-6,8-dimethyl-imidazo[1,2-a]pyrazin-3-yl)phenyl]cyclopropyl]methyl]-3-(p-tolylsulfonyl)urea |
| 7 | 1-[2-[4-(2-ethyl-6,8-dimethyl-imidazo[1,2-a]pyrazin-3-yl)phenyl]ethyl]-3-(4-fluorophenyl)sulfonyl-urea |
| 8 | 1-[2-[4-(2-ethyl-6,8-dimethyl-imidazo[1,2-a]pyridin-3-yl)phenyl]ethyl]-3-(p-tolylsulfonyl)urea |
| 9 | 1-[2-[4-[6,8-dimethyl-2-(trifluoromethy)pimidazo[1,2-a]pyrazin-3-yl]phenyl]ethyl]-3-(p-tolylsulfonyl)urea |
| 10 | 1-[2-[4-(2-cyclopropyl-6,8-dimethyl-imidazo[1,2-a]pyrazin-3-yl)phenyl]ethyl]-3(p-tolylsulfonyl)urea |

Experimental Procedures:

Synthesis

The following Examples illustrate the synthesis of representative compounds of formula (I). These examples are not intended, nor are they to be construed, as limiting the scope of the embodiments disclosed herein. It will be clear that various embodiments may be practiced otherwise than as particularly described herein. Numerous modifications and variations are possible in view of the teachings herein and, therefore, are within the scope.

Liquid chromatography-mass spectrometry (LCMS) experiments to determine retention times and associated mass ions were performed using one or more of the following Methods A, B, and C:

Method A: Waters BEH C18, 3.0×30 mm, 1.7 μm, was used at a temperature of 50° C. and at a flow rate of 1.5 mL/min, 2 μL injection, mobile phase: (A) water with 0.1% formic acid and 1% acetonitrile, mobile phase (B) MeOH with 0.1% formic acid; retention time given in minutes.

Method A details: (I) ran on a Binary Pump G1312B with UV/Vis diode array detector G1315C and Agilent 6130 mass spectrometer in positive and negative ion electrospray mode with UV PDA detection with a gradient of 15-95% (B) in a 2.2 min linear gradient (II) hold for 0.8 min at 95% (B) (III) decrease from 95-15% (B) in a 0.1 min linear gradient (IV) hold for 0.29 min at 15% (B);

Method B: An Agilent Zorbax Bonus RP, 2.1×50 mm, 3.5 μm, was used at a temperature of 50° C. and at a flow rate of 0.8 mL/min, 2 μL injection, mobile phase: (A) water with 0.1% formic acid and 1% acetonitrile, mobile phase (B) MeOH with 0.1% formic acid; retention time given in minutes.

Method B details: (I) ran on a Binary Pump G1312B with UV/Vis diode array detector G1315C and Agilent 6130 mass spectrometer in positive and negative ion electrospray mode with UV-detection at 220 and 254 nm with a gradient of 5-95% (B) in a 2.5 min linear gradient (II) hold for 0.5 min at 95% (B) (III) decrease from 95-5% (B) in a 0.1 min linear gradient (IV) hold for 0.29 min at 5% (B).

Method C: An API 150EX mass spectrometer linked to a Shimadzu LC-10AT LC system with a diode array detector was used. The spectrometer had an electrospray source operating in positive and negative ion mode. LC was carried out using an Agilent ZORBAX XDB 50×2.1 mm C18 column and a 0.5 mL/minute flow rate. Solvent A: 95% water, 5% acetonitrile containing 0.01% formic acid; Solvent B: acetonitrile. The gradient was shown as below. 0-0.5 min: 2% solvent (B); 0.5-2.5 min: 2% solvent B to 95% solvent (B); 2.5-4.0 min: 95% solvent (B); 4.0-4.2 min: 95% solvent (B) to 2% solvent B; 4.2-6.0 min: 2% solvent (B).

EXAMPLES

The following Examples provide a more detailed description of the process conditions for preparing compounds of the present invention. It is to be understood, however, that the invention, as fully described herein and as recited in the claims, is not intended to be limited by the details of the following schemes or modes of preparation.

Synthesis of Key Intermediate, tert-butyl N-[2-[4-(4,4,5,5-tetramethyl-1,3,2-dioxaborolan-2-yl)phenyl]ethyl]carbamate

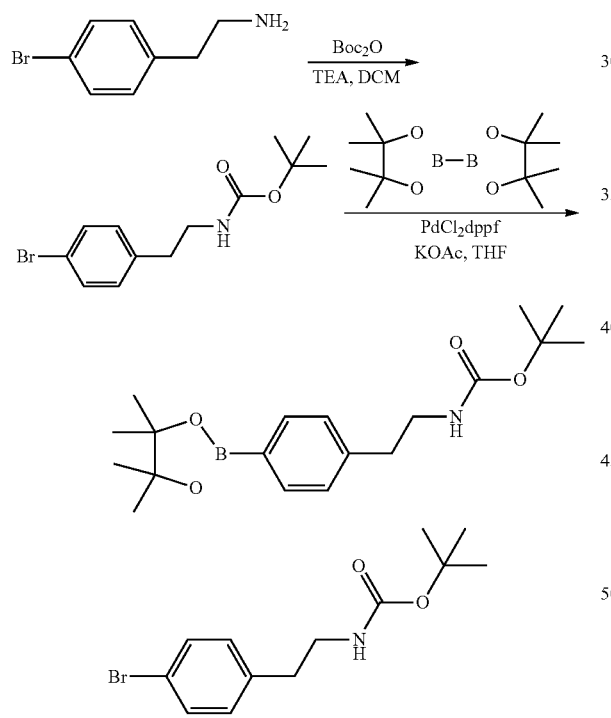

Intermediate 1: tert-butyl N-[2-(4-bromophenyl)ethyl]carbamate

Dissolved 2-(4-bromophenyl)ethanamine (25.0 g, 124.95 mmol) in DCM (500 mL). Charged with di-tert-butyl dicarbonate (32.7 g, 149.94 mmol) and triethylamine (52 mL, 373.08 mmol). Stirred at room temperature for 16 hours. Removed solvent and used crude without further purification.

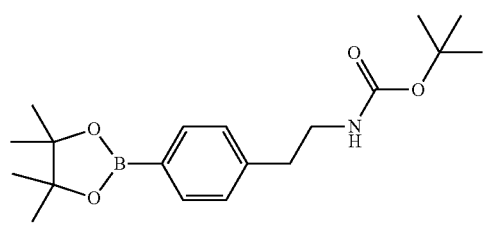 [SMILES: CC(C)(C)OC(=O)NCCc1ccc(B2OC(C)(C)C(C)(C)O2)cc1]

Intermediate 2: tert-butyl N-[2-[4-(4,4,5,5-tetramethyl-1,3,2-dioxaborolan-2-yl)phenyl]ethyl]carbamate Dissolved tert-butyl N-[2-(4-bromophenyl)ethyl]carbamate (~124.95 mmol) in THF (500 mL). Added bis(pinacolato)diboron (44.0 g, 174.93 mmol), palladium chloride diphenyl phosphine ferrocene (10.2 g, 10 mol %) and potassium acetate (36.8 g, 374.85 mmol). Heated to 65° C. for 16 hours. Removed solvent and purified using normal phase chromatography (0-100% EtOAc in heptanes) to yield 40.58 g of product; $^1$H NMR (400 MHz, CHLOROFORM-d) δ ppm 1.35 (s, 12H) 1.44 (s, 9H) 2.82 (t, J=6.74 Hz, 2H) 3.38 (d, J=5.86 Hz, 2H) 4.18-4.71 (m, 1H) 7.21 (d, J=7.42 Hz, 2H) 7.76 (d, J=7.61 Hz, 2H).

Example 1

Compound 1: 1-[2-[4-(2-ethyl-6,8-dimethyl-imidazo[1,2-a]pyrazin-3-yl)phenyl]ethyl]-3-(p-tolylsulfonyl)urea

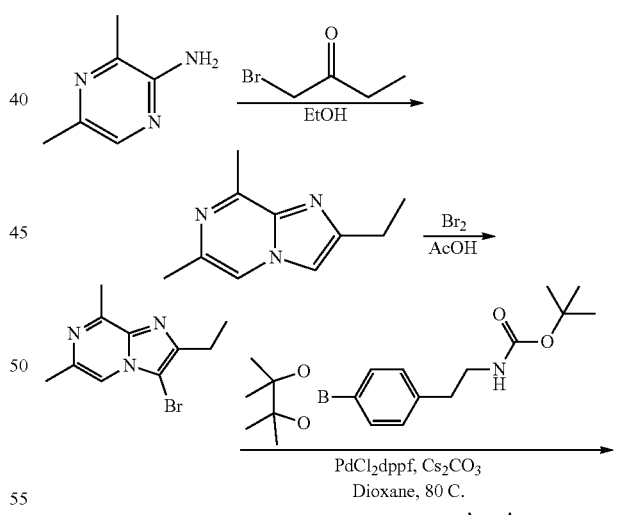

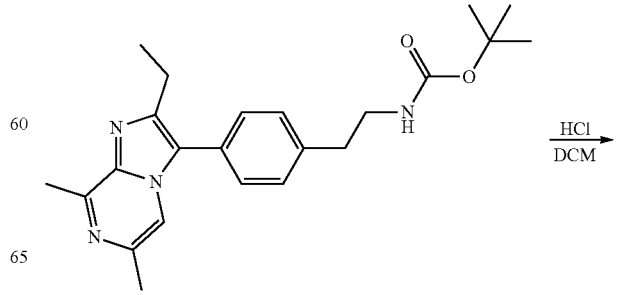

19

-continued

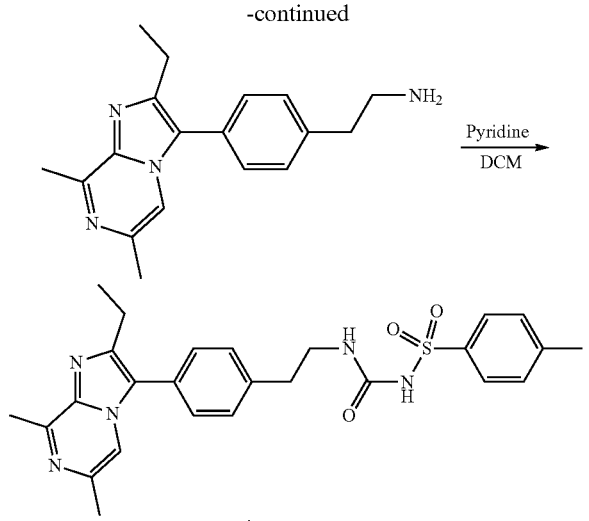

Intermediate 1: 2-ethyl-6,8-dimethyl-imidazo[1,2-a]pyrazine

Dissolved 3,5-dimethylpyrazin-2-amine (10.0 g, 81.7 mmol) in EtOH (500 mL). To this solution added 1-bromo-2-butanone (12.4 mL, 122 mmol). Heated to 65° C. for 16 hours. Removed the solvent in vacuo. Brought up residue in H₂O (500 mL) and extracted with EtOAc (3×500 mL). Washed the combined organics with brine and dried over Na₂SO₄. Filtered and removed solvent. Purified using normal phase chromatography (0-10% MeOH in DCM) to yield 8.7 g (49.5 mmol, 60%) of product; ¹H NMR (400 MHz, CHLOROFORM-d) δ=7.70 (s, 1H), 7.33 (s, 1H), 2.95-2.76 (m, 5H), 2.50-2.40 (m, 3H), 1.34 (t, J=7.6 Hz, 3H); LCMS (M/Z): 176.2 (M+H).

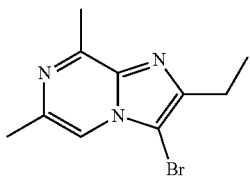

Intermediate 2: 3-bromo-2-ethyl-6,8-dimethyl-imidazo[1,2-a]pyrazine

Dissolved 2-ethyl-6,8-dimethyl-imidazo[1,2-a]pyrazine (15.1 g, 86.3 mmol) in acetic acid (500 mL). Slowly added bromine (4.4 mL, 86.3 mmol) to the solution and stirred at room temperature for two hours. Concentrated via vacuum and diluted with H₂O (400 mL). Adjusted pH to ~8 using NaHCO₃ (saturated). Extracted with EtOAc (3×500 mL) and purified using normal phase chromatography (0-10% MeOH in DCM) to yield 12.9 g (59%) of product; ¹H NMR (400 MHz, METHANOL-d₄) δ=8.01 (s, 1H), 2.86 (q, J=7.6 Hz, 2H), 2.81 (s, 3H), 2.52 (s, 3H), 1.34 (t, J=7.6 Hz, 3H); LCMS (M/Z): 254.0 (M+H).

20

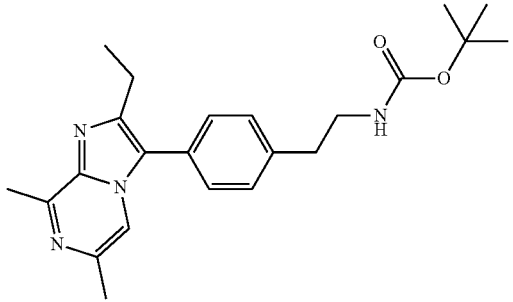 [SMILES: CCc1nc2c(C)nc(C)cn2c1-c1ccc(CCNC(=O)OC(C)(C)C)cc1]

Intermediate 3: tert-butyl N-[2-[4-(2-ethyl-6,8-dimethyl-imidazo[1,2-a]pyrazin-3-yl)phenyl]ethyl]carbamate Dissolved 3-bromo-2-ethyl-6,8-dimethyl-imidazo[1,2-a]pyrazine (12.6 g, 50.6 mmol) and tert-butyl N-[2-[4-(4,4,5,5-tetramethyl-1,3,2-dioxaborolan-2-yl)phenyl]ethyl]carbamate (21.1 g, 60.7 mmol) in 1,4-Dioxane (250 mL). Charged with palladium chloride diphenyl phosphine ferrocene (4.1 g, 10 mol %) and cesium carbonate (49.4 g, 151.6 mmol). Heated to 70° C. for 16 hours. Filtered through a silica plug and rinsed with 0-10% MeOH in DCM to yield 15.2 grams (38.6 mmol) of semi-crude product; LCMS (M/Z): 395.2 (M+H).

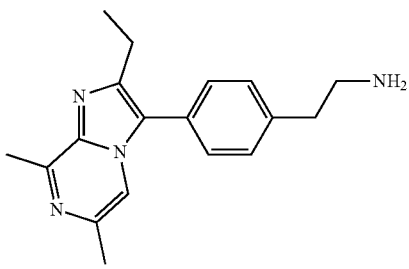 [SMILES: CCc1nc2c(C)nc(C)cn2c1-c1ccc(CCN)cc1]

Intermediate 4: 2-[4-(2-ethyl-6,8-dimethyl-imidazo[1,2-a]pyrazin-3-yl)phenyl]ethanamine Dissolved tert-butyl N-[2-[4-(2-ethyl-6,8-dimethyl-imidazo[1,2-a]pyrazin-3-yl)phenyl]ethyl]carbamate (15.2 g, 38.6 mmol) in DCM (300 mL) and cooled to 0° C. Slowly added trifluoracetic acid (30 mL, 390 mmol) to the solution. Allowed to warm to room temperature and stir for 16 hours. Neutralized to pH ~8 using NaHCO₃ (saturated). Collected organic. Washed the organic with brine and dried over Na₂SO₄. Filtered and removed solvent and purified using normal phase chromatography (0-10% MeOH in DCM) to yield 12.9 g (59%) of product; ¹H NMR (400 MHz, METHANOL-d₄) δ=7.82 (s, 1H), 7.61-7.43 (m, 4H), 3.19 (q, J=7.3 Hz, 2H), 3.12-3.00 (m, 2H), 2.88-2.71 (m, 5H), 2.38 (s, 3H), 1.36-1.27 (m, 3H); LCMS (M/Z): 295.2 (M+H).

21

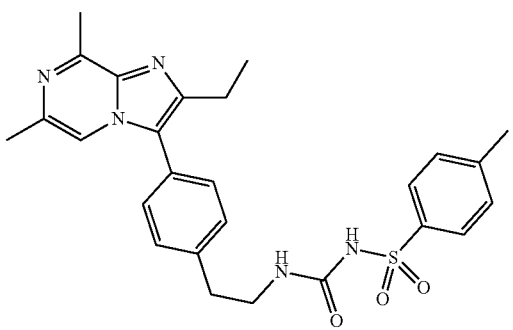

1-[2-[4-(2-ethyl-6,8-dimethyl-imidazo[1,2-a]pyrazin-3-yl)phenyl]ethyl]-3-(p-tolylsulfonyl)urea Dissolved 2-[4-(2-ethyl-6,8-dimethyl-imidazo[1,2-a]pyrazin-3-yl)phenyl]ethanamine (7.0 g, 23.8 mmol) in DCM (150 mL). Placed in an ice bath to cool to 0° C. Slowly added 4-toluenesulfonyl isocyanate (3.6 mL, 23.8 mmol) to the solution and stirred for 16 hours at room temperature. Removed solvent and purified using normal phase chromatography (0-10% MeOH in DCM) to yield 4.40 grams of product; $^1$H NMR (400 MHz, METHANOL-d$_4$) δ=7.81-7.75 (m, 1H), 7.37 (s, 4H), 7.31 (d, J=8.0 Hz, 2H), 3.41 (t, J=6.9 Hz, 2H), 2.92-2.70 (m, 7H), 2.37 (d, J=0.8 Hz, 3H), 2.33 (s, 3H), 1.26 (t, J=7.6 Hz, 3H); LCMS (M/Z): 492.2 (M+H).

Example 2

Compound 2: 1-[2-[4-(7-cyano-2-ethyl-6,8-dimethyl-imidazo[1,2-a]pyridin-3-yl)phenyl]ethyl]-3-(p-tolylsulfonyl)urea

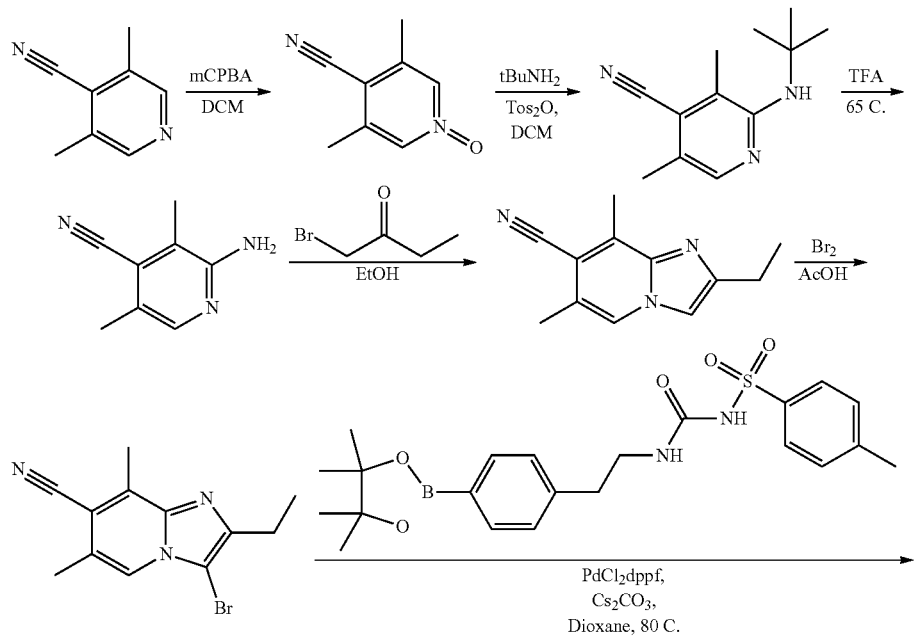

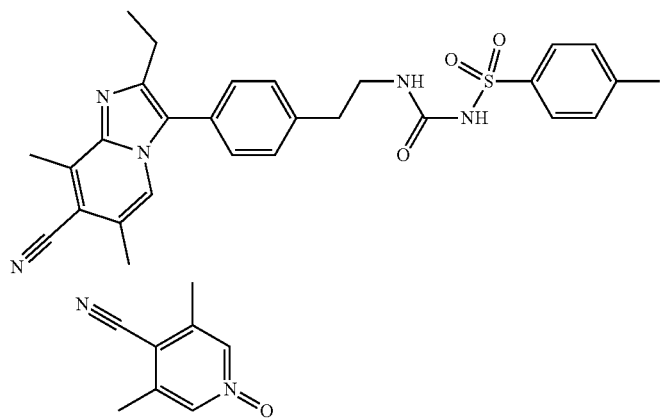

Intermediate 1: 3,5-dimethyl-1-oxo-pyridine-4-carbonitrile

Dissolved 3,5-dimethylpyridine-4-carbonitrile (1.57 g, 11.88 mmol) in DCM (100 mL). Charged with m-Chloroperbenzoic acid (4.10 g, 23.76 mmol). Stirred at room temperature for 16 hours. Washed the reaction mixture with NaHCO$_3$ (100 mL). Washed organic layer with brine and dried over Na$_2$SO$_4$. Filtered and removed solvent. Purified using normal phase chromatography (0-10% MeOH in DCM) to yield 1.57 g of product; $^1$H NMR (400 MHz, CHLOROFORM-d) δ ppm 2.48 (s, 6H) 8.01 (s, 2H); LCMS (M/Z): 149.2 (M+H).

Intermediate 2: 2-(tert-butylamino)-3,5-dimethyl-pyridine-4-carbonitrile

Dissolved 3,5-dimethyl-1-oxo-pyridine-4-carbonitrile (1.21 g, 8.17 mmol) in DCM (100 mL). Cooled to 0° C. and charged with tosic anhydride (5.33 g, 16.34 mmol). Stirred for 15 minutes. Added tert-butyl amine (4.29 mL, 40.85 mmol) and stirred an additional 15 minutes. Removed solvent and purified using normal phase conditions (0-100% EtOAc in Heptanes) to yield 720 mg of product; $^1$H NMR (400 MHz, CHLOROFORM-d) δ ppm 1.47 (s, 9H) 2.25 (s, 3H) 2.32 (s, 3H) 7.96 (s, 1H).

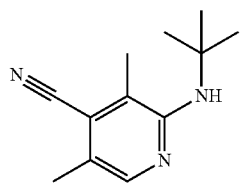

Intermediate 3: 2-amino-3,5-dimethyl-pyridine-4-carbonitrile

Dissolved 2-(tert-butylamino)-3,5-dimethyl-pyridine-4-carbonitrile (960 mg, 4.73 mmol) in trifluoroacetic acid (20 mL). Heated to 65° C. for 16 hours. Removed volatiles via rotovap. Brought up residue in NaHCO3 (1/2 sat'd, 40 mL). Large amount of solid crashed out of solution. Filtered off solid and dissolved in DCM (40 mL). Extracted aqueous with DCM (3×40 mL). Combined all organics and washed with brine. Dried over Na$_2$SO$_4$. Filtered and removed solvent to yield 640 mg of compound; $^1$H NMR (400 MHz, CHLOROFORM-d) δ ppm 2.33 (s, 3H) 2.36 (s, 3H) 7.93 (s, 1H); LCMS (M/Z): 148.2 (M+H).

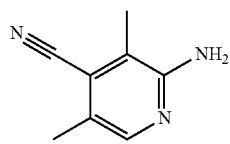

Intermediate 4: 2-amino-3,5-dimethyl-pyridine-4-carbonitrile

Dissolved 2-(tert-butylamino)-3,5-dimethyl-pyridine-4-carbonitrile (640 mg, 4.35 mmol) in EtOH (20 mL). Added 1-bromo-2-butanone (665 µL, 6.52 mmol). Heated the reaction to 65° C. and stirred for 16 hours. Removed solvent and brought up residue in NaHCO$_3$ (40 mL). Extracted with EtOAc (3×40 mL). Combined organics and washed with brine. Dried over Na$_2$SO$_4$. Filtered and removed solvent. Purified using normal phase chromatography (0-10% MeOH in DCM). Used the slightly impure product as is in next step; LCMS (M/Z): 200.2 (M+H).

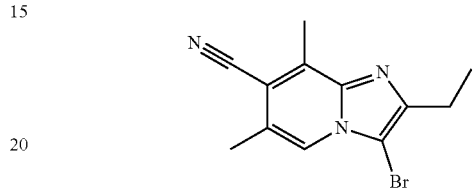

Intermediate 5: 3-bromo-2-ethyl-6,8-dimethyl-imidazo[1,2-a]pyridine-7-carbonitrile Dissolved 2-ethyl-6,8-dimethyl-imidazo[1,2-a]pyridine-7-carbonitrile (crude, ~4.35 mmol) in acetic acid (20 mL). Slowly added bromine (223 µL, 4.35 mmol) and stirred for 30 minutes. Concentrated via vacuum and diluted with H$_2$O (400 mL). Adjusted pH to ~8 using NaHCO$_3$ (sat'd). Collected the crude solid that crashed out of solution and washed with H$_2$O to yield 800 mg (2.88 mmol, 66% over two steps) of product; $^1$H NMR (400 MHz, CHLOROFORM-d) δ ppm 1.34 (t, J=7.61 Hz, 3H) 2.52 (s, 3H) 2.73-2.97 (m, 5H) 7.82 (s, 1H); LCMS (M/Z): 278.0 (M+H).

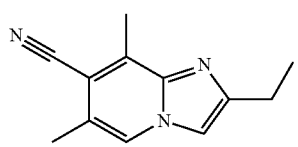

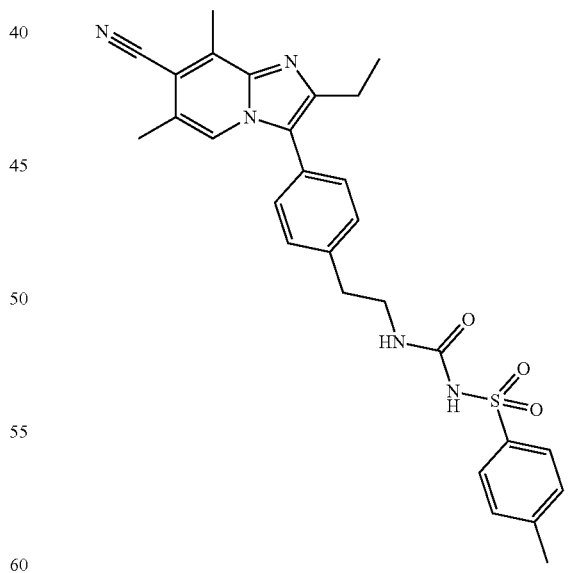

1-[2-[4-(7-cyano-2-ethyl-6,8-dimethyl-imidazo[1,2-a]pyridin-3-yl)phenyl]ethyl]-3-(p-tolylsulfonyl)urea Dissolved 3-bromo-2-ethyl-6,8-dimethyl-imidazo[1,2-a]pyridine-7-carbonitrile (100 mg, 0.360 mmol) and 1-(p- tolylsulfonyl)-3-[2-[4-(4,4,5,5-tetramethyl-1,3,2-dioxaborolan-2-yl)phenyl]ethyl]urea (240 mg, 0.540 mmol) in dioxane (3 mL). Charged with [1,1'-bis(diphenylphosphino) ferrocene]palladium(II) dichloride (30 mg, 10 mol %) and Cs$_2$CO$_3$ (586 mg, 1.80 mmol). Heated to 80° C. for 16 hours. Purified using normal phase chromatography (0-100% EtOAc in heptanes) to yield 42.5 mg of product; $^1$H NMR (400 MHz, CHLOROFORM-d) δ ppm 1.33 (t, J=7.52 Hz, 3H) 2.41 (d, J=2.34 Hz, 6H) 2.87 (q, J=7.42 Hz, 2H) 2.91-3.01 (m, 5H) 3.57 (q, J=6.70 Hz, 2H) 6.64-6.77 (m, 1H) 7.29 (d, J=8.20 Hz, 2H) 7.34-7.47 (m, 4H) 7.71 (d, J=8.20 Hz, 2H) 7.81 (s, 1H); LCMS (M/Z): 516.2 (M+H).

Example 3

Compound 3: 1-[2-[4-(2-ethyl-7-fluoro-6,8-dimethyl-imidazo[1,2-a]pyridin-3-yl)phenyl]ethyl]-3-(p-tolylsulfonyl)urea

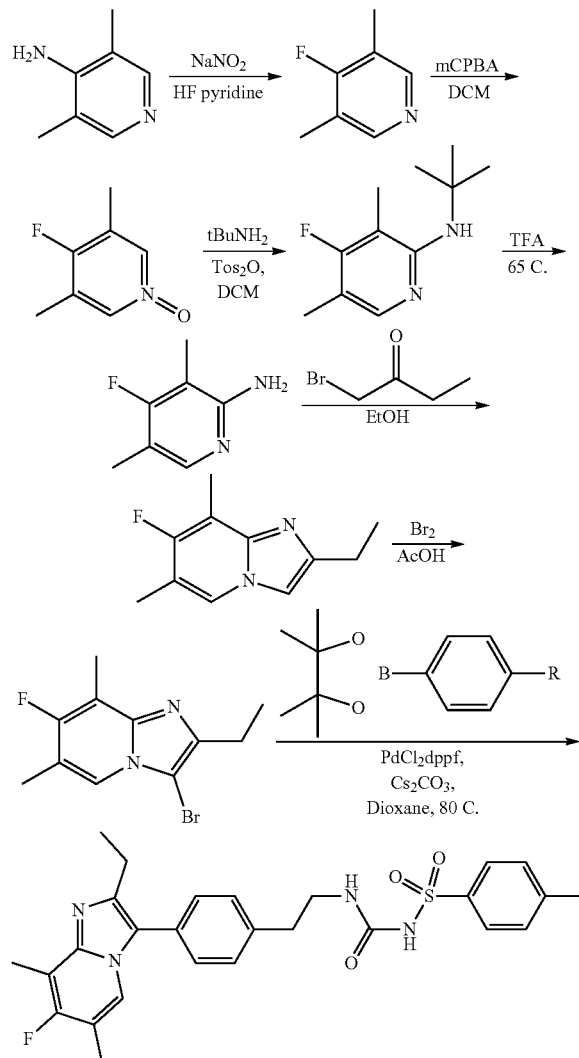

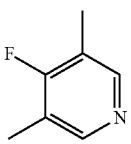

Intermediate 1: 4-fluoro-3,5-dimethyl-pyridine

Dissolved 3,5-dimethylpyridin-4-amine (5.0 g, 40.93 mmol) in HF pyridine (70%, 70 mL). Cooled to 0° C. and charged with sodium nitrite (4.23 g, 61.4 mmol). Allowed to warm to room temperature and stir for 16 hours. Removed solvent and purified using normal phase chromatography (0-10% MeOH in DCM). Used impure mixture as is for the next step. LCMS (M/Z): 126.2 (M+H).

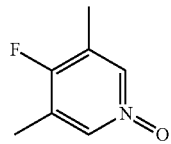

Intermediate 2: 4-fluoro-3,5-dimethyl-pyridine 1-oxide

Dissolved 4-fluoro-3,5-dimethyl-pyridine (~40.93 mmol) in DCM (200 mL). Charged with m-Chloroperbenzoic acid (10.59 g, 61.4 mmol). Stirred at room temperature for 16 hours. Washed the reaction mixture with NaHCO$_3$ (200 mL). Washed organic layer with brine and dried over Na$_2$SO$_4$. Filtered and removed solvent. Purified using normal phase chromatography (0-10% MeOH in DCM) to yield 1.00 g of product, plus additional 2.5 g of impure product; $^1$H NMR (400 MHz, DMSO-d$_6$) ☐ ppm 2.15 (d, J=1.56 Hz, 6H) 8.08 (d, J=6.05 Hz, 2H); LCMS (M/Z): 142.2 (M+H).

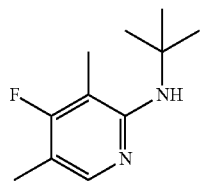

Intermediate 3: N-tert-butyl-4-fluoro-3,5-dimethyl-pyridin-2-amine

Dissolved 4-fluoro-3,5-dimethyl-pyridine 1-oxide (2.5 g, 17.71 mmol) in DCM (100 mL). Cooled to 0° C. and charged with tosic anhydride (6.75 g, 35.42 mmol). Stirred for 15 minutes. Added tert-butyl amine (9.3 mL, 88.56 mmol) and stirred for one hour. Removed solvent and used crude as is next step; 197.2 (M+H).

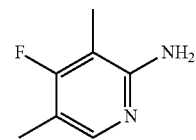

Intermediate 4: 4-fluoro-3,5-dimethyl-pyridin-2-amine

Dissolved N-tert-butyl-4-fluoro-3,5-dimethyl-pyridin-2-amine (17.71 mmol) in trifluoroacetic acid (40 mL). Heated to 65° C. for 2 hours. Removed volatiles via rotovap. Dissolved residue in NaHCO$_3$ (1/2 saturated, 40 mL). Extracted aqueous with DCM (3×40 mL). Combined organics and washed with brine. Dried over Na$_2$SO$_4$. Filtered and removed solvent. Used as is next step. LCMS (M/Z): 141.2 (M+H).

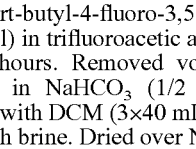

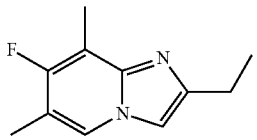

Intermediate 5: 2-ethyl-7-fluoro-6,8-dimethyl-imidazo[1,2-a]pyridine

Dissolved 4-fluoro-3,5-dimethyl-pyridin-2-amine (640 mg, 4.35 mmol) in EtOH (40 mL). Added 1-bromo-2-butanone (1.80 mL, 17.7 mmol). Heated the reaction to 80° C. and stirred for 16 hours. Removed solvent and dissolved residue in NaHCO$_3$ (40 mL). Extracted with EtOAc (3×40 mL). Combined organics and washed with brine. Dried over Na$_2$SO$_4$. Filtered and removed solvent. Purified using normal phase chromatography (0-10% MeOH in DCM). Used the slightly impure product as is in next step. Yield 400 mg; $^1$H NMR (400 MHz, METHANOL-d$_4$) δ ppm 1.43 (t, J=7.61 Hz, 3H) 2.41 (s, 3H) 2.54 (d, J=1.95 Hz, 3H) 2.93 (q, J=7.22 Hz, 2H) 7.89 (s, 1H) 8.54 (d, J=6.25 Hz, 1H); LCMS (M/Z): 193.2 (M+H).

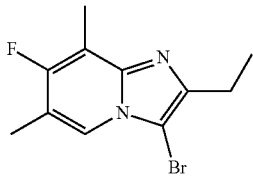

Intermediate 6: 3-bromo-2-ethyl-7-fluoro-6,8-dimethyl-imidazo[1,2-a]pyridine

Dissolved 2-ethyl-7-fluoro-6,8-dimethyl-imidazo[1,2-a]pyridine (200 mg, 1.04 mmol) in acetic acid (5 mL). Slowly added bromine (53 µL, 1.04 mmol) and stirred for 30 minutes. Concentrated via vacuum and diluted with H$_2$O (50 mL). Adjusted pH to ~8 using NaHCO$_3$ (sat'd). Extracted with EtOAc (3×50 mL). Washed with brine and dried over Na$_2$SO$_4$. Filtered and removed solvent. Purified using normal phase chromatography (0-10% MeOH in DCM) to yield 120 mg; $^1$H NMR (400 MHz, METHANOL-d$_4$) δ ppm 1.24-1.37 (m, 3H) 2.33 (s, 3H) 2.44 (d, J=2.15 Hz, 3H) 2.78 (q, J=7.61 Hz, 2H) 8.03 (d, J=6.83 Hz, 1H); LCMS (M/Z): 271.0 (M+H).

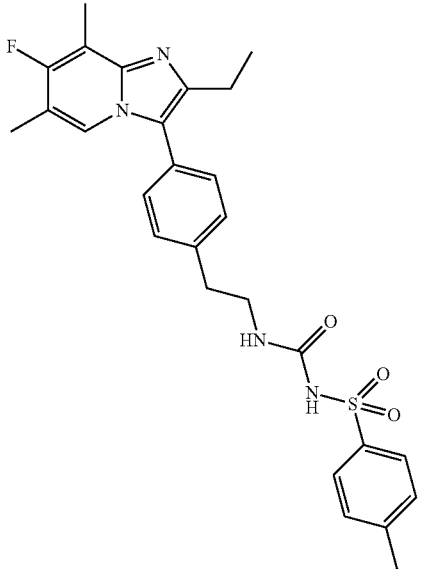 [SMILES: CCc1nc2c(C)c(F)c(C)cn2c1-c1ccc(CCNC(=O)NS(=O)(=O)c2ccc(C)cc2)cc1]

1-[2-[4-(2-ethyl-7-fluoro-6,8-dimethyl-imidazo[1,2-a]pyridin-3-yl)phenyl]ethyl]-3-(p-tolylsulfonyl)urea Dissolved 3-bromo-2-ethyl-7-fluoro-6,8-dimethyl-imidazo[1,2-a]pyridine (40 mg, 0.148 mmol) and 1-(p-tolylsulfonyl)-3-[2-[4-(4,4,5,5-tetramethyl-1,3,2-dioxaborolan-2-yl)phenyl]ethyl]urea (78 mg, 0.175 mmol) in Dioxane (1 mL). Charged with [1,1'-Bis(diphenylphosphino)ferrocene]palladium(II) dichloride (12 mg, 10 mol %) and Cs$_2$CO$_3$ (144 mg, 0.44 mmol). Heated to 80° C. for 1 hour using microwave. Purified using reverse phase chromatography (0-100% MeOH in H$_2$O) to yield 2.62 mg of product; $^1$H NMR (400 MHz, METHANOL-d$_4$) δ ppm 1.19-1.34 (m, 4H) 2.22 (s, 3H) 2.36 (s, 3H) 2.49 (d, J=1.76 Hz, 3H) 2.73 (d, J=7.42 Hz, 2H) 2.86 (s, 2H) 3.44 (s, 2H) 7.28-7.42 (m, 6H) 7.80 (d, J=8.20 Hz, 3H); LCMS (M/Z): 509.2 (M+H).

Example 4

Compound 4: 1-[2-[4-(2-ethyl-6,8-dimethyl-imidazo[1,2-a]pyrazin-3-yl)phenoxy]ethyl]-3-(p-tolylsulfonyl)urea

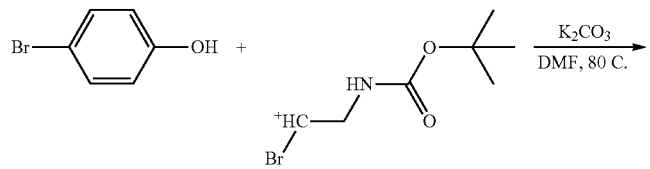

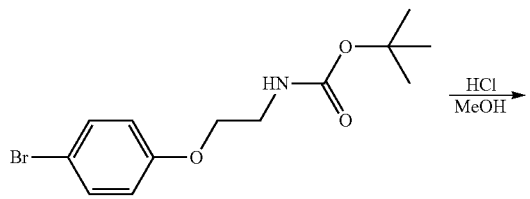

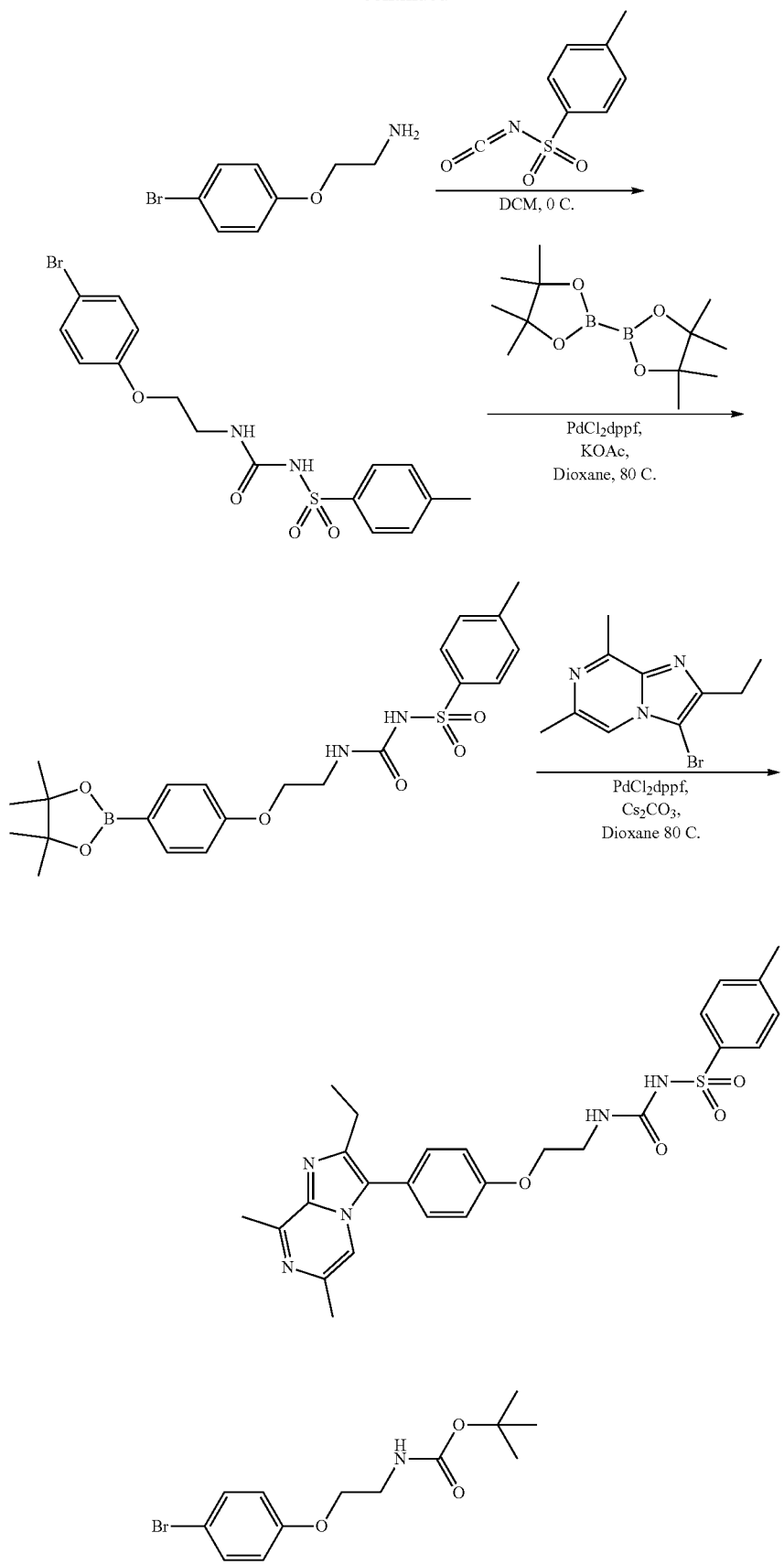

Intermediate 1: tert-butyl N-[2-(4-bromophenoxy)ethyl] carbamate Dissolved 4-bromophenol (2.32 g, 13.39 mmol) in DMF (100 mL). Charged with tert-butyl N-(2-bromoethyl)carbamate (3.00 g, 13.39 mmol) and K$_2$OC$_3$ (9.25 g, 66.93 mmol). Heated to 80° C. for 16 hours. Purified using normal phase conditions (0-40% EtOAc in heptanes) to isolate 3.31 grams of crude product; $^1$H NMR (400 MHz, METHANOL-d$_4$) δ ppm 1.46 (s, 9H) 3.44 (q, J=5.86 Hz, 2H) 4.00 (t, J=5.56 Hz, 2H) 6.85-6.96 (m, 2H) 7.40 (d, J=8.79 Hz, 2H); LCMS (M/Z): 218.2 (M+H).

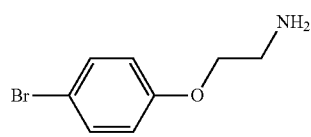 [SMILES: NCCOc1ccc(Br)cc1]

Intermediate 2: 2-(4-bromophenoxy)ethanamine

Dissolved tert-butyl N-[2-(4-bromophenoxy)ethyl]carbamate (3.31 g, 10.46 mmol) in MeOH (10 mL). Charged with HCl (3N in MeOH, 10 mL). Stirred at room temperature for 16 hours. Removed solvent and use crude as is next step.

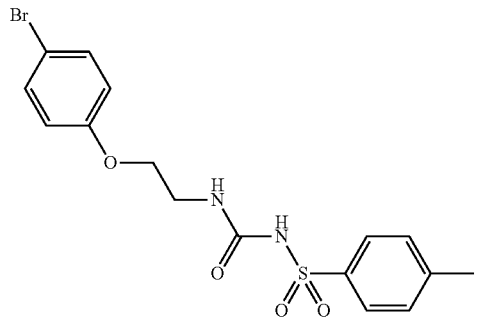 [SMILES: Cc1ccc(S(=O)(=O)NC(=O)NCCOc2ccc(Br)cc2)cc1]

Intermediate 3: 1-[2-(4-bromophenoxy)ethyl]-3-(p-tolylsulfonyl)urea

Dissolved 2-(4-bromophenoxy)ethanamine in DCM (50 mL). Cooled the solution to 0 C and slowly added 4-methylbenzenesulfonyl isocyanate (1.55 mL, 10.18 mmol). Allowed to warm to room temperature and stir for 2 hours. Collected white solid precipitate and washed with cold acetonitrile to yield 2.90 grams of desired product; $^1$H NMR (400 MHz, DMSO-d$_6$) δ ppm 2.30-2.43 (m, 3H) 3.32 (q, J=5.34 Hz, 3H) 3.90 (t, J=5.47 Hz, 2H) 6.67 (t, J=5.27 Hz, 1H) 6.86 (d, J=8.98 Hz, 2H) 7.36 (d, J=8.20 Hz, 2H) 7.43 (d, J=8.79 Hz, 2H) 7.76 (d, J=8.20 Hz, 2H); LCMS (M/Z): 415.0 (M+H).

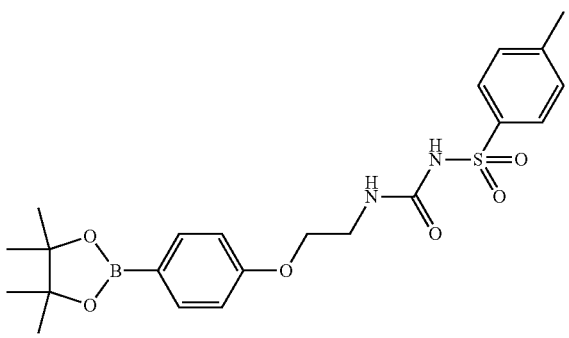

Intermediate 4: 1-(p-tolylsulfonyl)-3-[2-[4-(4,4,5,5-tetramethyl-1,3,2-dioxaborolan-2-yl)phenoxy]ethyl]urea Dissolved 1-[2-(4-bromophenoxy)ethyl]-3-(p-tolylsulfonyl)urea (1.50 g, 3.63 mmol) in Dioxane (20 mL). Charged with Bis(pinacolato)diboron (1.11 g, 4.39 mmol), with [1,1'-Bis(diphenylphosphino)ferrocene]palladium(II) dichloride (296 mg, 10 mol %) and potassium acetate (1.78 g, 18.15 mmol). Heated to 80° C. for 16 hours. Purified using normal phase chromatography (0-10% MeOH in DCM) to yield 1.14 g of crude product; LCMS (M/Z): 461.2 (M+H).

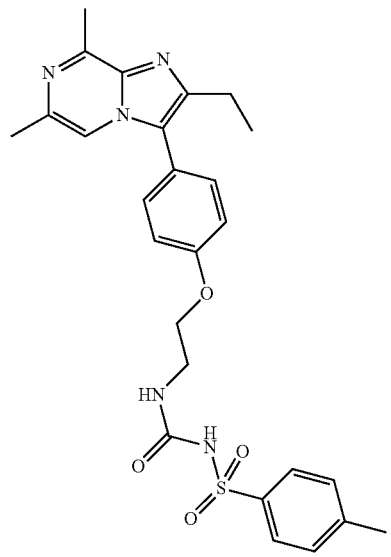

1-[2-[4-(2-ethyl-6,8-dimethyl-imidazo[1,2-a]pyrazin-3-yl)phenoxy]ethyl]-3-(p-tolylsulfonyl)urea Dissolved 3-bromo-2-ethyl-6,8-dimethyl-imidazo[1,2-a]pyrazine (60 mg, 0.235 mmol) and 1-(p-tolylsulfonyl)-3-[2-[4-(4,4,5,5-tetramethyl-1,3,2-dioxaborolan-2-yl)phenoxy]ethyl]urea (130 mg, 0.282 mmol) in Dioxane (3 mL). Charged with [1,1'-Bis(diphenylphosphino) ferrocene]palladium(II) dichloride (19 mg, 10 mol %) and Cs$_2$CO$_3$ (382 mg, 1.17 mmol). Heated to 80° C. for 16 hours. Purified using reverse phase chromatography (0-100% MeOH in H$_2$O) to yield 5.3 mg of product; $^1$H NMR (400 MHz, METHANOL-d$_4$) δ ppm 1.30 (t, J=7.61 Hz, 3H) 2.40 (d, J=11.71 Hz, 6H) 2.76-2.90 (m, 6H) 3.57 (s, 2H) 4.08 (s, 2H) 7.15 (d, J=8.59

Hz, 2H) 7.30 (d, J=8.00 Hz, 2H) 7.43 (d, J=8.59 Hz, 2H) 7.81-7.90 (m, 3H); LCMS (M/Z): 508.2 (M+H).

Example 5

Compound 5: 1-[2-[4-(2-ethyl-6,8-dimethyl-imidazo[1,2-a]pyrazin-3-yl)phenyl]-2-methyl-propyl]-3-(p-tolylsulfonyl)urea

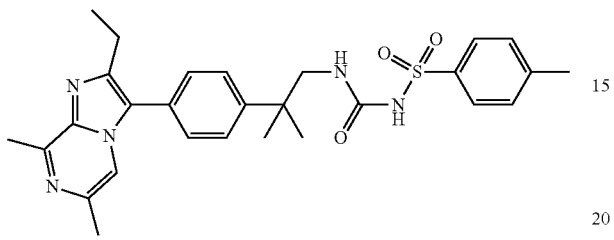

1-[2-[4-(2-ethyl-6,8-dimethyl-imidazo[1,2-a]pyrazin-3-yl)phenyl]-2-methyl-propyl]-3-(p-tolylsulfonyl)urea Followed methods analogous to those in previous examples.

$^1$H NMR (500 MHz, METHANOL-d4) δ=7.79-7.41 (m, 8H), 7.31 (br s, 1H), 5.50 (br s, 2H), 3.55-3.34 (m, 8H), 2.84 (br s, 3H), 2.51-2.20 (m, 3H), 1.55-1.09 (m, 6H); LCMS (M/Z): 520.2 (M+H).

Example 6

Compound 6: 1-[[1-[4-(2-ethyl-6,8-dimethyl-imidazo[1,2-a]pyrazin-3-yl)phenyl]cyclopropyl]methyl]-3-(p-tolylsulfonyl)urea

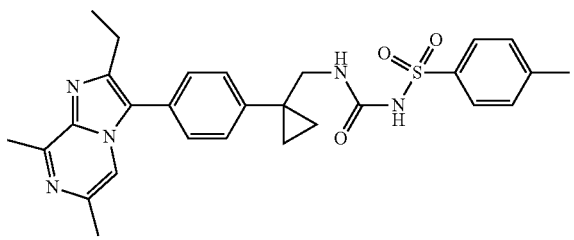

1-[[1-[4-(2-ethyl-6,8-dimethyl-imidazo[1,2-a]pyrazin-3-yl)phenyl]cyclopropyl]methyl]-3-(p-tolylsulfonyl)urea Followed methods analogous to those in previous examples.

$^1$H NMR (400 MHz, METHANOL-d4) δ=7.82 (s, 1H), 7.77-7.71 (m, 2H), 7.47 (br d, J=8.2 Hz, 2H), 7.35 (d, J=8.2 Hz, 2H), 7.26 (br d, J=8.2 Hz, 2H), 3.39 (s, 2H), 2.88-2.71 (m, 5H), 2.48-2.33 (m, 3H), 2.30-2.17 (m, 3H), 1.28 (t, J=7.6 Hz, 3H), 0.91 (br d, J=1.0 Hz, 4H); LCMS (M/Z): 518.2 (M+H).

Example 7

Compound 7: 1-[2-[4-(2-ethyl-6,8-dimethyl-imidazo[1,2-a]pyrazin-3-yl)phenyl]ethyl]-3-(4-fluorophenyl)sulfonyl-urea

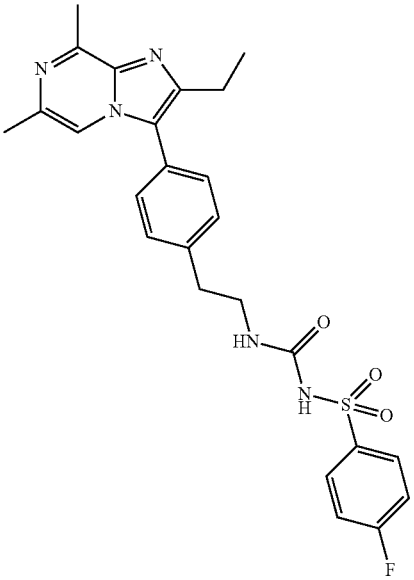 [SMILES: CCc1nc2c(C)nc(C)cn2c1-c1ccc(CCNC(=O)NS(=O)(=O)c2ccc(F)cc2)cc1]

1-[2-[4-(2-ethyl-6,8-dimethyl-imidazo[1,2-a]pyrazin-3-yl)phenyl]ethyl]-3-(4-fluorophenyl)sulfonyl-urea Dissolved 2-[4-(2-ethyl-6,8-dimethyl-imidazo[1,2-a]pyrazin-3-yl)phenyl]ethanamine (100 mg, 0.34 mmol) in DCM (2 mL). Placed in an ice bath to cool to 0° C. Slowly added 4-fluorobenzene sulfonyl isocyanate (68.4 mg, 0.34 mmol) to the solution and stir for 16 hours at room temperature. Removed solvent and purified using normal phase chromatography (0-10% MeOH in DCM) to yield 59.6 milligrams of product; $^1$H NMR (400 MHz, METHANOL-d$_4$) δ=8.07 (s, 1H), 8.02-7.89 (m, 2H), 7.52-7.38 (m, 4H), 7.25 (t, J=8.8 Hz, 2H), 3.40 (t, J=7.0 Hz, 2H), 2.94 (s, 3H), 2.91-2.79 (m, 4H), 2.49 (s, 3H), 1.31 (t, J=7.5 Hz, 3H); LCMS (M/Z): 496.2 (M+H).

Example 8

Compound 8: 1-[2-[4-(2-ethyl-6,8-dimethyl-imidazo[1,2-a]pyridin-3-yl)phenyl]ethyl]-3-(p-tolylsulfonyl)urea

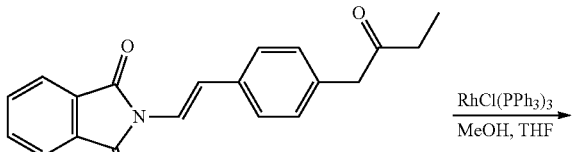

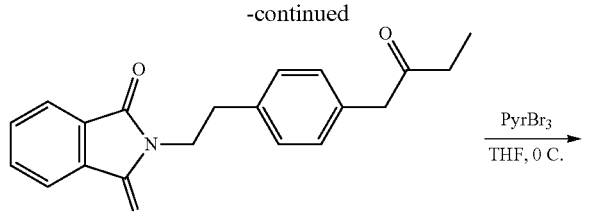

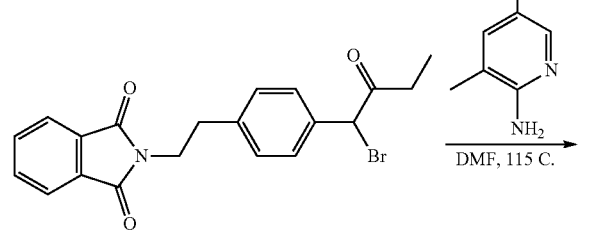

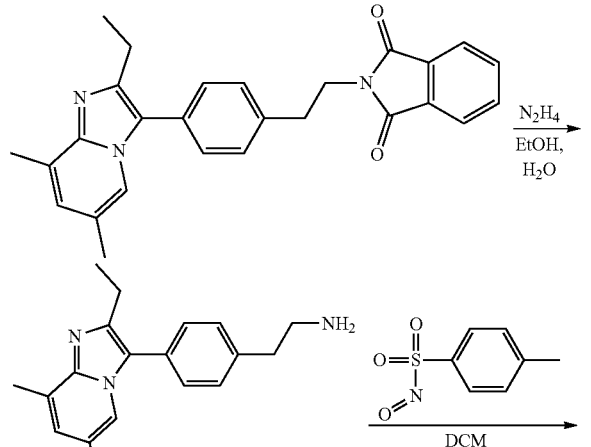

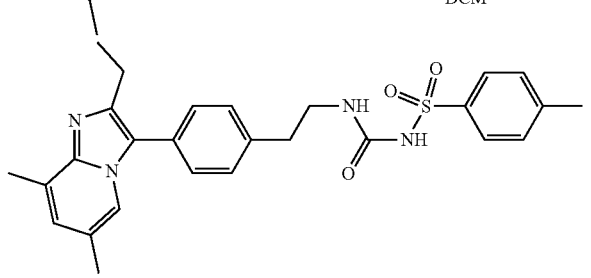

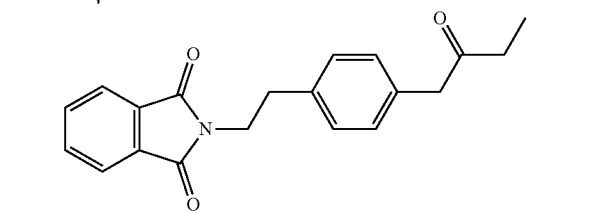

Intermediate 1: 2-[2-[4-(2-oxobutyl)phenyl]ethyl]isoindoline-1,3-dione

Dissolved 2-[(E)-2-[4-(2-oxobutyl)phenyl]vinyl]isoindoline-1,3-dione (2.1 g, 6.58 mmol) in THF (400 mL). Added Wilkinson's catalyst (0.39 g, 0.426 mmol) to the solution. Charged with H₂ and stirred for 16 hours. Reaction only obtained partial conversion. Filtered reaction through a pad of celite and concentrated under vacuum. Dissolved residue in EtOAc (100 mL) and passed through a pad of silica. Rinsed silica with EtOAc (3×20 mL). Concentrated under vacuum. Dissolved residue in THF (100 mL). Added Wilkinson's catalyst (420 mg, 0.45 mmol) to the solution. Charged with H₂ and stirred for 16 hours. Filtered through a pad of celite. Rinsed celite with THF (3×25 mL) and combined organics. Concentrated under vacuum. Dissolved residue in EtOAc and filtered through a pad of silica. Rinsed silica with EtOAc (3×25 mL). Concentrated organics and purified using normal phase chromatography (0-40% EtOAc in Heptanes) to yield 1.84 grams of compound.

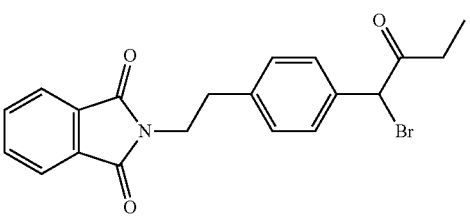 [SMILES: CCC(=O)C(Br)c1ccc(CCN2C(=O)c3ccccc3C2=O)cc1]

Intermediate 2: 2-[2-[4-(1-bromo-2-oxo-butyl)phenyl]ethyl]isoindoline-1,3-dione

Dissolved 2-[2-[4-(2-oxobutyl)phenyl]ethyl]isoindoline-1,3-dione (184 mg, 0.573 mmol) in THF (mL). Cooled to 0° C. and added pyridinium tribromide (183 mg, 0.573 mmol). Stirred at 0° C. for 25 minutes. Diluted with H₂O (20 mL) and extracted with EtOAc (50 mL). Washed the organic layer with Na₂S₂O₃ (saturated) and brine. Dried over Na₂SO₄, filtered and removed solvent. Purified using normal phase chromatography (0-0.5% EtOAc in DCM) to give a mixture of bromides (3.6: 1, 186 mg).

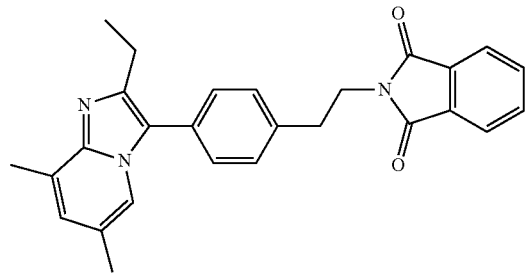 [SMILES: CCc1nc2c(C)cc(C)cn2c1-c1ccc(CCN2C(=O)c3ccccc3C2=O)cc1]

Intermediate 3: 2-[2-[4-(2-ethyl-6,8-dimethyl-imidazo[1,2-a]pyridin-3-yl)phenyl]ethyl]isoindoline-1,3-dione Dissolved 2-[2-[4-(1-bromo-2-oxo-butyl)phenyl]ethyl]isoindoline-1,3-dione (480 mg, 1.199 mmol) in DMF (9.5 mL) and charged with 3,5-dimethylpyradin-2-amine (147 mg, 1.199 mmol). Heated to 115 C for 2.5 hours. Diluted with EtOAc (50 mL) and washed with NaHCO3 (saturated, 20 mL), H2O (3×20 mL) and brine (20 mL). Dry over Na2SO4, filtered and removed solvent. Purified using normal phase conditions (0-100% EtOAc in Heptanes) to yield 179.4 mg of product; ¹H NMR (400 MHz, CHLOROFORM-d) δ ppm 1.28 (t, J=7.52 Hz, 3H) 2.22 (s, 3H) 2.54-2.67 (m, 3H) 2.78 (q, J=7.55 Hz, 2H) 3.04-3.19 (m, 2H) 3.95-4.09 (m, 2H) 6.81 (s, 1H) 7.32-7.38 (m, 2H) 7.39-7.47 (m, 2H) 7.64 (s, 1H) 7.73 (dd, J=5.37, 3.03 Hz, 2H) 7.81-7.91 (m, 2H).

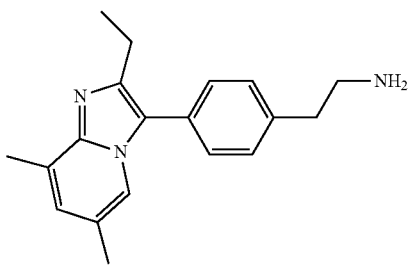 [SMILES: CCc1nc2c(C)cc(C)cn2c1-c1ccc(CCN)cc1]

Intermediate 4: 2-[4-(2-ethyl-6,8-dimethyl-imidazo[1,2-a]pyridin-3-yl)phenyl]ethanamine Dissolved 2-[2-[4-(2-ethyl-6,8-dimethyl-imidazo[1,2-a]pyridin-3-yl)phenyl]ethyl]isoindoline-1,3-dione (85.6 mg, 0.202 mmol) in EtOH (3.8 mL). Charged with hydrazine (50-60%, 1 mL). Heated the reaction mixture to 78 C for 45 minutes. Concentrated under vacuum and bring up residue in 1N NaOH solution (10 mL). Extracted with EtOAc (6×20 mL). Combined organics and washed with brine. Dried over $Na_2SO_4$, filtered and removed solvent. Purified using normal phase chromatography (0-100% MeOH in DCM) to yield 59.6 mg of product; $^1$H NMR (400 MHz, CHLOROFORM-d) δ ppm 1.31 (t, J=7.52 Hz, 3H) 1.68 (br. s., 2H) 2.22 (s, 3H) 2.62 (s, 3H) 2.73-2.92 (m, 4H) 3.02-3.13 (m, 2H) 6.81 (s, 1H) 7.32-7.44 (m, 4H) 7.69 (s, 1H).

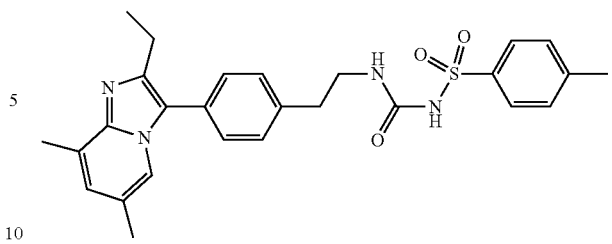

1-[2-[4-(2-ethyl-6,8-dimethyl-imidazo[1,2-a]pyridin-3-yl)phenyl]ethyl]-3-(p-tolylsulfonyl)urea Dissolved 2-[4-(2-ethyl-6,8-dimethyl-imidazo[1,2-a]pyridin-3-yl)phenyl]ethanamine (56.5 mg, 0.193 mmol) in DCM (4 mL). Charged with toluene sulfonyl isocyanate (0.0294 mL, 0.193 mmol). Stirred for 3 hours at room temperature. Removed solvent and purified using normal phase chromatography (0-15% MeOH in DCM) to yield 78.4 mg of product; $^1$H NMR (400 MHz, DMSO-$d_6$) δ ppm 1.21 (t, J=7.52 Hz, 3H) 2.19 (s, 3H) 2.34 (s, 3H) 2.47 (s, 3H) 2.65 (q, J=7.61 Hz, 2H) 2.74 (t, J=7.13 Hz, 2H) 3.22-3.29 (m, 2H) 6.91 (s, 1H) 7.20-7.44 (m, 6H) 7.67-7.87 (m, 3H).

Example 9

Compound 9: 1-[2-[4-[6,8-dimethyl-2-(trifluoromethyl)imidazo[1,2-a]pyrazin-3-yl]phenyl]ethyl]-3-(p-tolylsulfonyl)urea

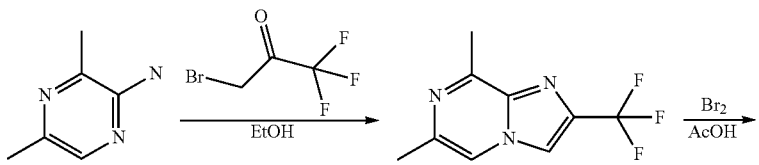

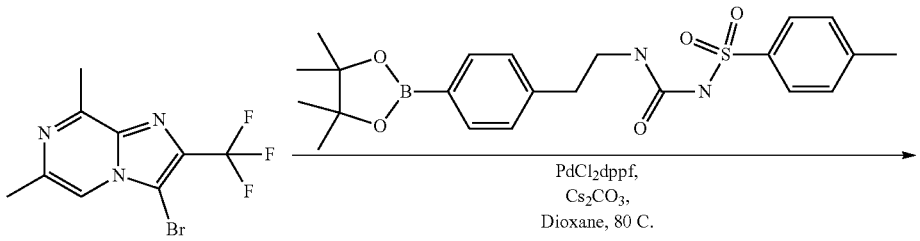

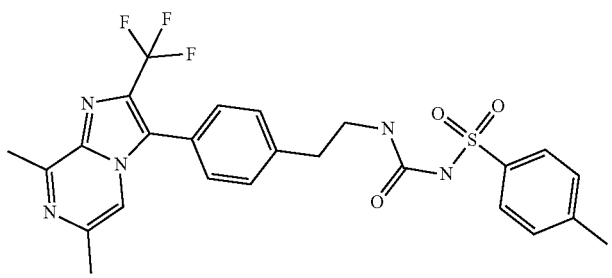

Followed methods analogous to those in previous examples. Then, 3-bromo-6,8-dimethyl-2-(trifluoromethyl)imidazo[1,2-a]pyrazine (0.5 mmol, 146.5 mg) and 1-(p-tolylsulfonyl)-3-[2-[4-(4,4,5,5-tetramethyl-1,3,2-dioxaborolan-2-yl)phenyl]ethyl]urea (0.75 mmol, 333.0 mg) were taken in Dioxane (5.0 ml) and water (2.0 ml) and the solution was degassed for 3 min. A degassed solution of cesium carbonate (1.5 mmol, 487.0 mg) in water (2.0 ml) was added followed by Pd(dppf)$_2$Cl$_2$:DCM (81.6 mg). The mixture was degassed again for 5 min and the reaction was stirred at 80° C. for 2 h. LC-MS indicated completion of reaction. The reaction was cooled and diluted with ethyl acetate (20 ml) and filtered through celite and concentrated. The crude was purified on silica gel using heptane/ethyl acetate to give 177 mg (0.33 mmol, 65%) of the desired product. LC-MS 532 (M+H); $^1$H NMR (400 MHz, METHANOL-d4) δ ppm 2.35 (s, 3H) 2.39 (d, J=0.83 Hz, 3H) 2.79-2.90 (m, 5H) 3.42 (t, J=6.98 Hz, 2H) 7.32 (d, J=8.00 Hz, 2H) 7.35-7.45 (m, 4H) 7.73 (s, 1H) 7.78 (d, J=8.40 Hz, 2H).

Example 10

Compound 10: 1-[2-[4-(2-cyclopropyl-6,8-dimethyl-imidazo[1,2-a]pyrazin-3-yl)phenyl]ethyl]-3-(p-tolylsulfonyl)urea

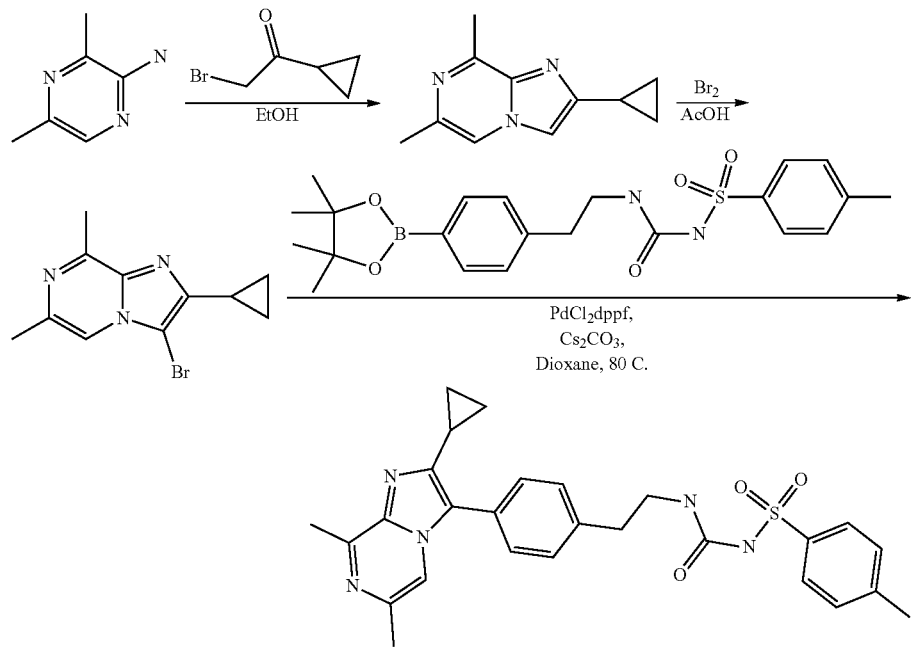

Followed methods analogous to those used in previous examples. Then, 3-bromo-2-cyclopropyl-6,8-dimethyl-imidazo[1,2-a]pyrazine (0.5 mmol, 132.5 mg) and 1-(p-tolylsulfonyl)-3-[2-[4-(4,4,5,5-tetramethyl-1,3,2-dioxaborolan-2-yl)phenyl]ethyl]urea (0.75 mmol, 333.0 mg) were taken in Dioxane (5.0 ml) and water (2.0 ml) and the solution was degassed for 3 min. A degassed solution of cesium carbonate (1.5 mmol, 487.0 mg) in water (2.0 ml) was added followed by Pd(dppf)$_2$Cl$_2$:DCM (81.6 mg). The mixture was degassed again for 5 min and the reaction was stirred at 80° C. for 2 h. LC-MS indicated completion of reaction. The reaction was cooled and diluted with ethyl acetate (20 ml) and filtered through celite and concentrated. The crude was purified on silica gel using heptane/ethyl acetate to give 126 mg (0.25 mmol, 50%) of the desired product.

LC-MS 504 (M+H); $^1$H NMR (400 MHz, METHANOL-d4) δ ppm 0.79-1.18 (m, 4H) 1.93-2.10 (m, 1H) 2.31 (s, 3H) 2.36 (s, 3H) 2.76 (s, 3H) 2.83 (t, J=6.96 Hz, 2H) 3.41 (t, J=6.96 Hz, 2H) 7.30 (d, J=8.15 Hz, 2H) 7.35-7.40 (m, 2H) 7.42-7.50 (m, 2H) 7.71-7.84 (m, 3H).

Evaluation

The biological activity of compounds of the present invention was tested using the test methods described below.

Compounds were assayed at Eurofins Cerep using the human EP4 receptor antagonist screen. Cellular antagonist effect was calculated as a % inhibition of control reference agonist response for each target (PGE2). In each EP4(h) experiment, a reference antagonist compound, GW627-368X, was tested concurrently with the test compounds, and the data were compared with historical values determined at Eurofins. The experiments were accepted in accordance with Eurofins validation Standard Operating Procedure.

| Assay | Source | Stimulus Receptors | Incubation | Measured Component | Detection Method |
|---|---|---|---|---|---|
| EP$_4$(h) (antagonist effect) | human recombinant (CHO cells) | PGE$_2$ (30 nM) | 10 min RT | cAMP | HTRF |

The results are provided: the compounds of the invention generally have greater than 50% inhibition at 1000 nM.

Preferred compounds of the invention, such as compounds 1-4 and 6-10 have about 50% or greater inhibition at 100 nM.

All publications, patents and patent applications cited in this specification are incorporated herein by reference for the teaching to which such citation is used.

Test compounds for the experiments described herein were employed in free or salt form.

The specific responses observed may vary according to and depending on the particular active compound selected or whether there are present carriers, as well as the type of formulation and mode of administration employed, and such expected variations or differences in the results are contemplated in accordance with practice of the present invention.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

The invention claimed is:

1. A compound 1-[2-[4-(2-ethyl-6,8-dimethylimidazo[1,2-a]pyrazin-3-yl)phenyl]ethyl]-3-(p-tolylsulfonyl)urea of the formula:

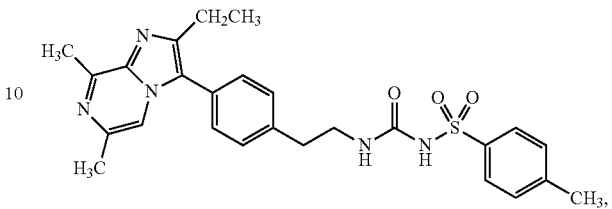

or a veterinary or pharmaceutically acceptable salt thereof.

2. A veterinary or pharmaceutical composition comprising the compound of claim 1 and one or more veterinary or pharmaceutically acceptable carriers.

\* \* \* \* \*

UNITED STATES PATENT AND TRADEMARK OFFICE
CERTIFICATE OF CORRECTION

PATENT NO. : 10,239,885 B1
APPLICATION NO. : 16/100315
DATED : March 26, 2019
INVENTOR(S) : Jason D. Speake It is certified that error appears in the above-identified patent and that said Letters Patent is hereby corrected as shown below:

On the Title Page

Item (54), should read as follows:
--A COMPOUND 1-[2-[4-(2-ETHYL-6,8-DIMETHYLIMIDAZO[1,2-α]PYRAZIN-3-YL)PHENYL]ETHYL]-3-(p-TOLYLSULFONYL)UREA AS A PROSTAGLANDIN EP4 RECEPTOR ANTAGONIST--

Item (57), the Abstract, should read as follows:
--The present invention describes novel compounds, or veterinary or pharmaceutically acceptable salts thereof, veterinary or pharmaceutical compositions thereof, and medical uses thereof. The compounds of the invention have activity as prostaglandin EP4 receptor antagonists and are useful in the treatment or alleviation of pain, inflammation and inflammation-associated disorders. Also described herein are methods for treating pain by administering the compounds of the invention. For example, the invention describes
-[2-[4-(2-ethyl-6,8-dimethyl-imidazo[1,2-α]pyrazin-3-yl)phenyl]ethyl]-3-(p-tolylsulfonyl)urea of the formula:

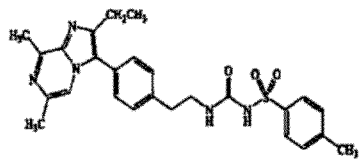

veterinary or pharmaceutical compositions thereof, and methods of treatment using the subject compound and compositions thereof.--

Signed and Sealed this
Sixteenth Day of July, 2019

Andrei Iancu
*Director of the United States Patent and Trademark Office*